United States Patent
Bocchi et al.

(10) Patent No.: US 10,571,475 B2
(45) Date of Patent: Feb. 25, 2020

(54) RAPID SCREENING OF MONOCLONAL ANTIBODIES

(75) Inventors: Massimo Bocchi, Sasso Marconi (IT); Roberto Guerrieri, Bologna (IT)

(73) Assignee: Cellply S.R.L., Bologna (IT)

( * ) Notice: Subject to any disclaimer, the term of this patent is extended or adjusted under 35 U.S.C. 154(b) by 468 days.

(21) Appl. No.: 13/991,379

(22) PCT Filed: Dec. 5, 2011

(86) PCT No.: PCT/EP2011/071820
§ 371 (c)(1),
(2), (4) Date: Jun. 3, 2013

(87) PCT Pub. No.: WO2012/072823
PCT Pub. Date: Jun. 7, 2012

(65) Prior Publication Data
US 2013/0252258 A1    Sep. 26, 2013

Related U.S. Application Data

(60) Provisional application No. 61/419,543, filed on Dec. 3, 2010.

(51) Int. Cl.
*G01N 33/53* (2006.01)
*G01N 33/68* (2006.01)
*G01N 33/536* (2006.01)

(52) U.S. Cl.
CPC ......... *G01N 33/6854* (2013.01); *G01N 33/53* (2013.01); *G01N 33/5302* (2013.01); *G01N 33/5304* (2013.01); *G01N 33/536* (2013.01)

(58) Field of Classification Search
None
See application file for complete search history.

(56) References Cited

U.S. PATENT DOCUMENTS

| 4,747,919 A | 5/1988 | Anderson |
|---|---|---|
| 5,496,697 A | 3/1996 | Parce et al. |
| 5,589,047 A | 12/1996 | Coster et al. |
| 5,814,668 A | 9/1998 | Whittemore et al. |

(Continued)

FOREIGN PATENT DOCUMENTS

| CN | 101460253 A | 6/2009 |
|---|---|---|
| EP | 1088592 A2 | 4/2001 |

(Continued)

OTHER PUBLICATIONS

Bocchi M et al, "Electronic Microsystems for Handling of Rare Cells", IEEE Transactions on Electron Devices, IEEE Service Center, Pisacataway, NJ, US, (Jan. 1, 2010), vol. 57, No. 1, doi:10.1109/TED.2009.2035026, ISSN 0018-9383, p. 244-255.*

(Continued)

*Primary Examiner* — Christopher L Chin
(74) *Attorney, Agent, or Firm* — Meunier Carlin & Curfman LLC

(57) ABSTRACT

Methods and systems for rapid and efficient screening of monoclonal antibodies and antibody-secreting cells, and particularly of single antibody-secreting cells, for both primary and functional characteristics, and particularly cell to cell interactions, in a microfluidic system, in particular an inverted open microwell system, where the particle(s) is not bound to a substrate.

11 Claims, 9 Drawing Sheets

(56) References Cited

U.S. PATENT DOCUMENTS

| | | | |
|---|---|---|---|
| 5,846,396 | A | 12/1998 | Zanzucchi et al. |
| 6,610,188 | B1 | 8/2003 | Fuhr et al. |
| 6,652,809 | B1 | 11/2003 | Comley et al. |
| 6,716,629 | B2 | 4/2004 | Hess et al. |
| 6,932,893 | B2 | 8/2005 | Bech et al. |
| 6,942,776 | B2 | 9/2005 | Medoro |
| 7,018,819 | B2 | 3/2006 | Orwar et al. |
| 7,081,189 | B2 | 7/2006 | Squires et al. |
| 7,189,578 | B1 | 3/2007 | Feng et al. |
| 7,238,268 | B2 | 7/2007 | Ramsey et al. |
| 7,776,553 | B2 | 8/2010 | Love et al. |
| 8,388,823 | B2 | 3/2013 | Manaresi et al. |
| 9,039,883 | B2 | 5/2015 | Guerrieri et al. |
| 9,816,910 | B2 | 11/2017 | Bocchi et al. |
| 2002/0036139 | A1 | 3/2002 | Becker et al. |
| 2002/0053399 | A1 | 5/2002 | Soane et al. |
| 2002/0092767 | A1 | 7/2002 | Bjornson et al. |
| 2002/0125139 | A1 | 9/2002 | Chow et al. |
| 2002/0142482 | A1 | 10/2002 | Wu et al. |
| 2002/0182627 | A1 | 12/2002 | Wang et al. |
| 2002/0182657 | A1 | 12/2002 | Ranger |
| 2002/0182749 | A1 | 12/2002 | Singh et al. |
| 2003/0039585 | A1 | 2/2003 | Freeman |
| 2003/0087309 | A1 | 5/2003 | Chen |
| 2003/0104588 | A1 | 6/2003 | Orwar et al. |
| 2004/0011652 | A1 | 1/2004 | Bressler |
| 2004/0175708 | A1 | 9/2004 | Caillat et al. |
| 2005/0058990 | A1 | 3/2005 | Guia et al. |
| 2005/0139473 | A1 | 6/2005 | Washizu et al. |
| 2006/0029955 | A1 | 2/2006 | Guia et al. |
| 2006/0196772 | A1* | 9/2006 | Kim .................. B03C 5/026 204/547 |
| 2006/0199173 | A1 | 9/2006 | Thielecke et al. |
| 2006/0231405 | A1 | 10/2006 | Hughes et al. |
| 2007/0243523 | A1* | 10/2007 | Ionescu-Zanetti ..... C12M 41/36 435/4 |
| 2008/0067068 | A1 | 3/2008 | Li |
| 2008/0210558 | A1 | 9/2008 | Sauter-Starace et al. |
| 2009/0107907 | A1 | 4/2009 | Chen et al. |
| 2009/0258383 | A1* | 10/2009 | Kovac ............... B01L 3/502761 435/29 |
| 2009/0288963 | A1* | 11/2009 | Guerrieri ................ B03C 5/005 205/792 |
| 2010/0152054 | A1 | 6/2010 | Love et al. |
| 2012/0034623 | A1 | 2/2012 | Hulsken et al. |
| 2013/0068618 | A1 | 3/2013 | Harrer et al. |
| 2013/0134040 | A1 | 5/2013 | Lee et al. |
| 2013/0252258 | A1* | 9/2013 | Bocchi .............. G01N 33/6854 435/7.21 |
| 2013/0256137 | A1 | 10/2013 | Holt |
| 2013/0261021 | A1* | 10/2013 | Bocchi .................. B01L 3/5088 506/9 |
| 2015/0209786 | A1 | 7/2015 | Hage et al. |
| 2016/0161392 | A1 | 6/2016 | Ionescu-Zanetti et al. |
| 2016/0178502 | A1 | 6/2016 | Bocchi et al. |
| 2018/0043357 | A1 | 2/2018 | Bocchi et al. |

FOREIGN PATENT DOCUMENTS

| | | | |
|---|---|---|---|
| EP | 1185373 | B1 | 3/2002 |
| EP | 1390467 | B1 | 2/2004 |
| WO | WO199962622 | A1 | 9/1999 |
| WO | 1999062622 | A1 | 12/1999 |
| WO | WO2001009297 | A1 | 2/2001 |
| WO | 2002088300 | A1 | 11/2002 |
| WO | WO 2007/138464 | A2 * | 12/2007 |
| WO | WO 2007138464 | A2 * | 12/2007 ............. B03C 5/005 |
| WO | WO2007138464 | A2 | 12/2007 |
| WO | WO2009151505 | A1 | 12/2009 |
| WO | WO 2010085275 | A1 * | 7/2010 ......... G01N 33/5047 |
| WO | 2010135468 | A1 | 11/2010 |
| WO | WO2012072822 | A1 | 6/2012 |
| WO | WO2012072823 | A1 | 6/2012 |

OTHER PUBLICATIONS

Konry et al. ("Droplet-based microfluidic platforms for single T cell secretion analysis of IL-10 cytokine" Biosens Bioelectron. Jan. 15, 2011; 26(5): 2707-2710. Published online Sep. 15, 2010 doi:10.1016/j.bios.2010.09.006).*

Lucas et al., "Lab-on-a-chip immunoassay for multiple antibodies using microsphere light scattering and quantum dot emission", Biosensors and Bioelectronics, Elsevier BV, NL, (Nov. 15, 2007), vol. 23, No. 5, doi:10.1016/J.BIOS.2007.08.004, ISSN 0956-5663, p. 675-681.*

Jin et al., "A rapid and efficient single-cell manipulation method for screening antigen-specific antibody-secreting cells from human peripheral blood", Nature Medicine, (2009), vol. 15, doi:doi:10.1038/nm.1966, p. 1088-1092, XP002573901.*

Bocchi et al. ("Inverted open microwells for cell trapping, cell aggregate formation and parallel recovery of live cells" Lab Chip, 2012, 12, 3168-3176).*

Faenza et al. ("Impedance measurement technique for high-sensitivity cell detection in microstructures with non-uniform conductivity distribution" Lab Chip, 2012, 12, 2046-2052).*

Bocchi et al. ("Dielectrophoretic trapping in microwells for manipulation of single cells and small aggregates of particles" Biosensors and Bioelectronics 24 (2009) 1177-1183).*

Dura et al. ("Spatially and temporally controlled immune cell interactions using microscale tools" Current Opinion in Immunology 2015, 35:23-29).*

Bocchi et al. ("Inverted open microwells for analysis and functional sorting of single live cells" 15th International Conference on Miniaturized Systems for Chemistry and Life Sciences Oct. 2-6, 2011, Seattle, Washington, USA).*

Park et al. ("High-throughput single-cell quantification using simple microwell-based cell docking and programmable time-course live-cell imaging" Lab Chip, 2011, 11, 79-86).*

International Search Report and Written Opinion issued in PCT/EP2011/071820, dated Mar. 30, 2012, 11 pages.

"Apoptosis, Cell Death, and Cell Proliferation—3rd Edition," Roche Applied Science, 174pp (NPL uploaded in 5 parts).

Bessette, Paul H., et al., "Microfluidic Library Screening for Mapping Antibody Epitopes," Analytical Chemistry, vol. 79, No. 5, Mar. 1, 2007, pp. 2174-2178, XP55022596.

Bhat, Rauf et al., "Serial Killing of Tumor Cells by Human Natural Killer Cells—Enhancement by Therapeutic Antibodies", PLOS One, vol. 2, No. 3, 2007, e326, 7 pages.

Bocchi, Massimo et al., "Electronic Microsystems for Handling of Rare Cells," IEEE Transactions on Electron Devices, vol. 57, No. 1, Jan. 1, 2010, pp. 244-255.

Duqi, E. et al., "Automated isolation of a programmable number of cells into microwells using DEP forces and optical detection", International Conference on Microtechnologies in Medicine and Biology, May 2011, 2 pages.

Faenza, A. et al., "Controlled isolation and patterning of K562 leukemia cells using electrically activated microchannels", International Conference on Microtechnologies in Medicine and Biology, May 2011.

Faenza, Andrea et al., "Continuous Impedance Monitoring of Single Cells Delivered in Open Microwell Arrays", presented at the 13th International Conference on Miniaturized Systems for Chemistry and Life Sciences, Nov. 1-5, 2009, Jeju, Korea, 3 pages.

Han et al., "Integration of single oocyte trapping, in vitro fertilization and embryo culture in a microwell-structured microfluidic device", Lab on a Chip, vol. 10, No. 21, 2010, pp. 2848-2854.

International Search Report and Written Opinion issued in PCT/EP2011/071819, dated May 4, 2012, 14 pages.

Jin, Aishun et al., "A rapid and efficient single-cell manipulation method for screening antigen-specific antibody-secreting cells from human peripheral blood" Nature Medicine, vol. 15, 2009, pp. 1088-1092.

Lucas, et al. "Lab-on-a-chip Immunoassay for Multiple Antibodies Using Microsphere Light Scattering and Quantum Dot Emission," Biosensors and Bioelectronics, Elsevier BV, NL, vol. 23, No. 5, Nov. 15, 2007, pp. 675-681, XP022345923.

(56) References Cited

OTHER PUBLICATIONS

Neri, Simona et al., "Calcein-Acetyoxymethyl Cytotoxicity Assay: Standardization of a Method Allowing Additional Analyses on Recovered Effector Cells and Supermatants", Clinical and Diagnostic Laboratory Immunology, Nov. 2011, vol. 8, No. 6 pp. 1131-1135.
Rastogi, Vinayak, et al., "Development and Evaluation of Realistic Microbiosassays in Freely Suspended Dropletson a Chip," Biomicrofluids, AIP, US, Online, vol. 1, No. 1, Mar. 1, 2007, pp. 14107-1, XP008149939.
Ronan, J.L. et al., "Optimization of the surfaces used to capture antibodies from single hybridomas reduces the time required for microengraving" J. Immunol. Methods, vol. 340, No. 2, Jan. 2009, pp. 164-169.
Anderson, Melvin, et al. "Recent Advances in 2D and 3D In Vitro Systems Using Primary Hepatocytes, Alternative Hepatocyte Sources and Non-Parenchymal Liver Cells and Their Use in Investigating Mechanisms of Hepatotoxicity, Cell Signaling and ADME." Arch. Toxicol., Review Article, 87:1315-1530, 2013.
Au, Anthony K., et al. "Review: Microvalves and Micropumps for BioMEMS." Micromachines, 2:179-220, 2011.
Bernards, Rene and Van't Veer, Laura J. "Enabling Personalized Cancer Medicine Through Analysis of Gene-Expression Patterns" Nature, 452(3):564-570, May 2008.
Dai, MingHua and Copley, Shelley D. Genome Shuffling Improves Degradation of the Anthropogenic Pesticide Pentachlorophenol by Sphingobium Chlorophenolicum ATCC 39723. Applied and Environmental Microbiology, 70 (4):2391-2397, Apr. 2004.
El-Ali, Jamil et al. "Cells on Chips." Nature, vol. 442, Jul. 27, 2006. 9 pages.
Fabian, Ina and Kravtsov, Vladimir D. "Automated Monitoring of Apoptosis in Suspension Cell Cultures." Laboratory Investigation, 74(2):557-570, 1996.
Higashiyama, Kenichi et al. "Dielectric Analysis for Estimation of Oil Content in the Mycelia of Mortierella Alpina." Biotechnology and Bioengineering, vol. 65, No. 5, Dec. 5, 1999. 6 pages.

International Search Report and Written Opinion issued in Italian Application No. 102016000061106, dated Feb. 9, 2017, 10 pages, including English translation of Written Opinion.
International Search Report and Written Opinion issued in PCT/IB2007/001427, completed Nov. 13, 2007, 7 pages.
Khine, Michelle, et al. "A Single Cell Electroporation Chip." The Royal Society of Chemistry, Lab on a Chip, vol. 5:38-43, 2005.
Lin, Yu-Cheng, et al. "A Microchip for Electroporation of Primary Endothelial Cells." Sensors and Actuators A 108:12-19, 2003.
Majumder, Biswanath, et al. "Predicting Clinical Response to Anticancer Drugs Using an Ex Vivo Platform That Captures Tumour Heterogeneity." Nature Communications, 6:6169, Feb. 27, 2015, pp. 1-14.
Matsudaira, Paul. "Intrahelical Ion Pairs in Intermediate Filaments." Proc. Natl. Acad. Sci. USA, Commentary, vol. 92, p. 86, Jan. 1995.
Muller, Torsten et al. "The Potential of Dielectrophoresis for Single-Cell Experiments." IEEE Engineering in Medicine and Biology Magazine. Nov./Dec. 2003. 12 pages.
Salter, Russel D. and Cresswell, Peter. "Impaired Assembly and Transport of HLA-A and -B Antigens in a Mutant TxB Cell Hybrid." The EMBO Journal, 5(5): 943-949, 1986.
Sohn, L. L., et al. "Capacitance Cytometry: Measuring Biological Cells One by One." PNAS, 97(20):10687-10690, Sep. 26, 2000.
Staunton, Jane E., et al. "Chemosensitivity Prediction by Transcriptional Profiling." PNAS, 98(19):10787-10792, Sep. 11, 2001.
Stromberg, Anette et al. "Microfluidic Device for Combinatorial Fusion of Liposomes and Cells." Analytical Chemistry, vol. 73, No. 1, Jan. 1, 2001. 6 pages.
Thielecke, Hagen, et al. "A Multicellular Spheroid-Based Sensor for Anti-Cancer Therapeutics." Biosensors & Electronics, 16:261-269, 2001.
Tian, C., et al. "Evaluation of a Chemoresponse Assay as a Predictive Marker in the Treatment of Recurrent Ovarian Cancer: Further Analysis of a Propsective Study." British Journal of Cancer, 111:843-850, 2014.
Weisenthal, Larry M. "A Novel Dye Exclusion Method for Testing in Vitro Chemosensitivity of Human Tumors." Cancer Research, 43:749-757, Feb. 1983.

\* cited by examiner

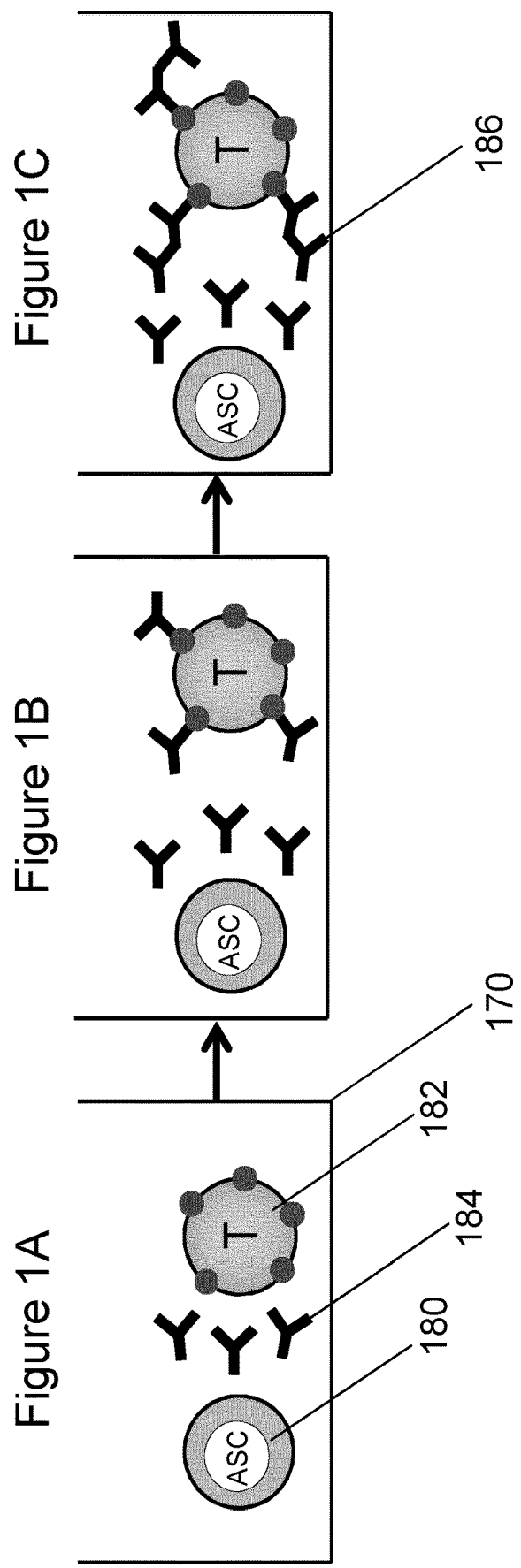

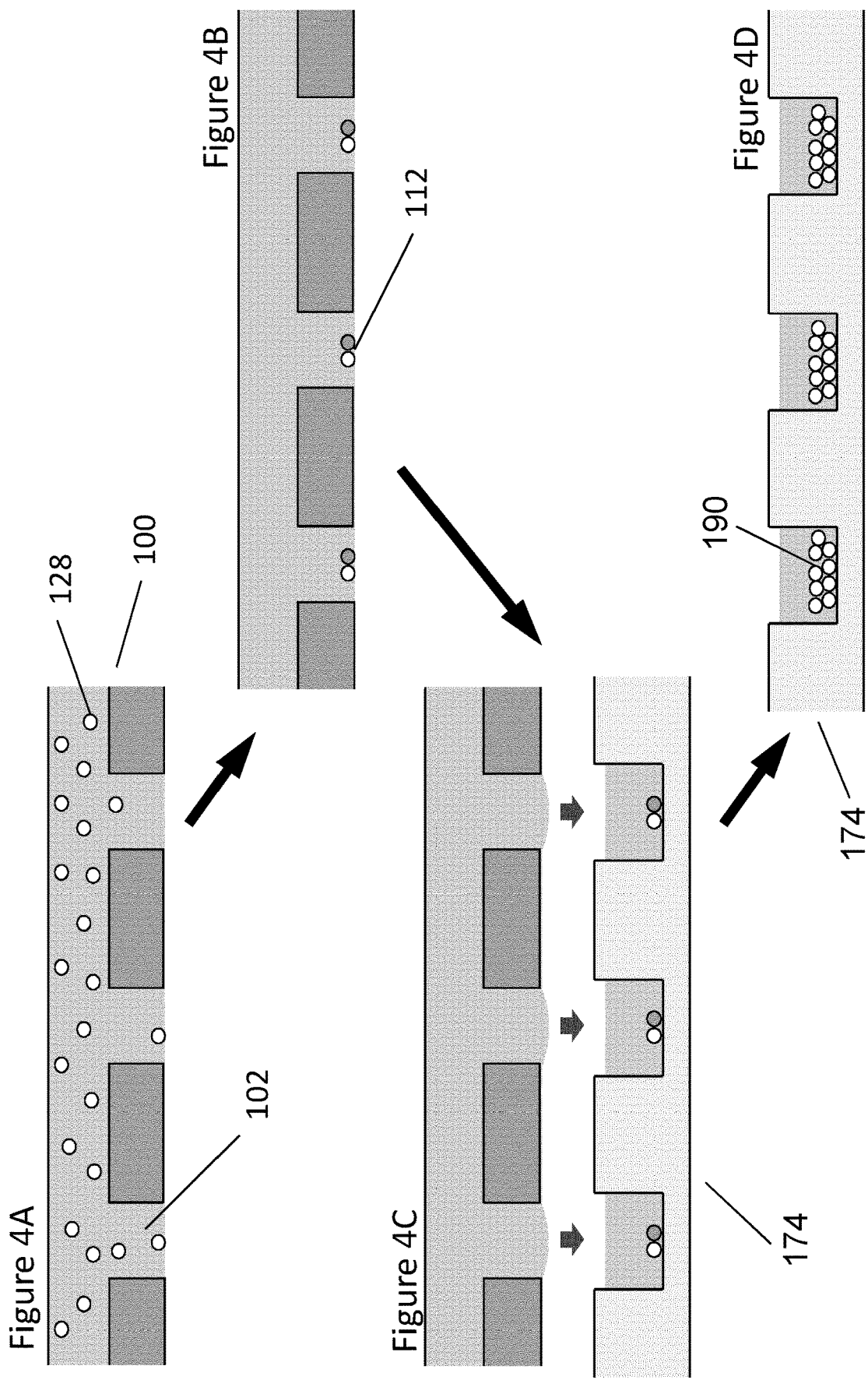

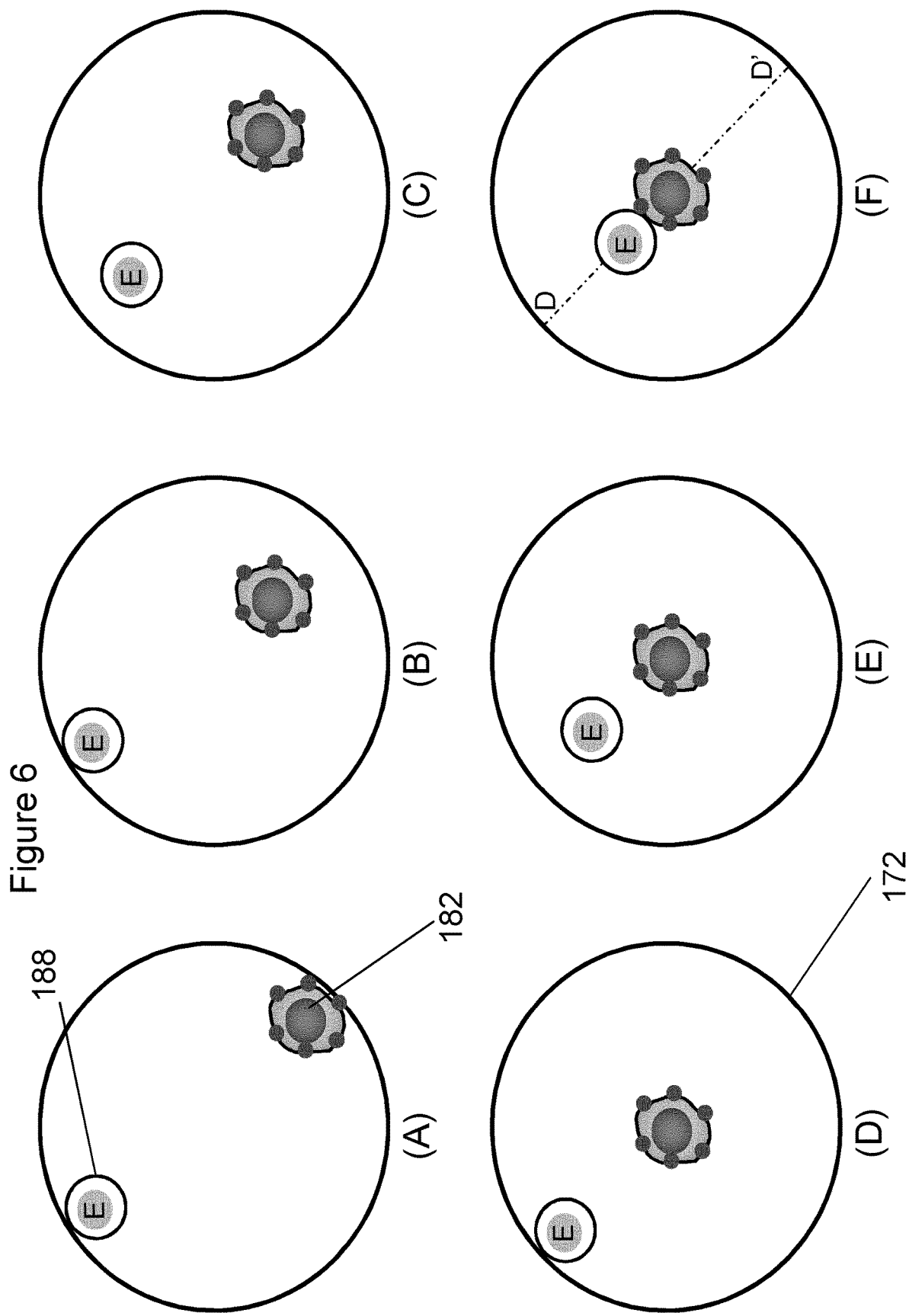

RAPID SCREENING OF MONOCLONAL ANTIBODIES

CROSS-REFERENCE TO RELATED APPLICATIONS

This application is a U.S. national phase application, filed pursuant to 35 U.S.C. § 371, of PCT application No. PCT/EP2011/071820, entitled "Rapid Screening of Monoclonal Antibodies," filed Dec. 5, 2011, which claims the benefit of U.S. Provisional Application No. 61/419,543, entitled "Rapid Screening of Monoclonal Antibodies", filed Dec. 3, 2010, which are herein incorporated by reference in their entireties for all purposes.

BACKGROUND OF THE INVENTION

Therapeutic molecules such as antibodies are valuable tools in today's treatment of various disorders, including treatment of cancers and immune disorders. The process of screening immune cells to identify potential therapeutic antibody candidates generally begins with the identification and isolation of antibodies and/or antibody-secreting cells (ASC) producing antibodies that bind specifically and with high affinity to a desired antigen. The process can include generation and random evaluation of very large phage display libraries, isolation of antibody secreting cells from human samples or transgenic mice, and/or high throughput screening of antibody binding to a selected target. This screening is only a first step in a laborious process that seeks to identify those antibody secreting cells producing antibodies with high binding affinity and specificity to a target antigen, but also able to trigger the cellular responses necessary for the diagnosis and treatment of disease. Rapid and efficient analytical systems and methods for screening both binding and functional activities are needed to advance the pace of drug discovery and development.

The in vitro evaluation of antibody function is based on complex interactions among antibodies, immune cells, and target cells, and generally requires large amounts of antibody from each candidate antibody-secreting cell. To obtain sufficient material, the candidate cells may be immortalized and expanded. This not only delays functional screening by several months, it also causes expensive and time consuming analyses of many potential antibodies and/or antibody-secreting cells that will not ultimately be of therapeutic value.

There is a need for methods and systems for screening of particles, for example immune cells such as antibody secreting cells, in a rapid and efficient manner that leads to early identification of candidate therapeutic molecules having useful functional properties for therapeutic product development.

SUMMARY OF THE INVENTION

Methods and systems are disclosed herein that provide rapid and efficient functional screening of molecules and cells, for example, by analyzing single cells in a micro-sized environment. In particular, the disclosed methods include functional screening of antibodies and antibody secreting cells (ASC), for example, by placing one or more particle, including single cells and non-cell particles, in contact or in close proximity to detect a specific antibody-induced response by the deposited cells and non-cell particles. In an embodiment, single cells, cell pairs, or small functional aggregates of cells and non-cell particles are particularly deposited at a location within a microwell for rapid and efficient detection of a response induced by an antibody such as a monoclonal antibody. The antibody can be delivered to the deposited cells through a fluid feeding the microwell or can be produced at the location by an antibody secreting cell. Cells are delivered and deposited at a particular location using methods to ensure contact or close proximity, thereby enabling analysis of cellular interactions.

In an embodiment, antibody secreting cells are screened to identify those cells producing antibodies with useful binding and functional characteristics. Such characteristics include binding specificity and affinity of antibodies for target antigens, including target cells, as well as functional screening of cellular activities, such as apoptosis, cytolysis or cytotoxicity induced by an effector cell or complement proteins on a target cell and mediated by the presence of an antibody such as a monoclonal antibody. As demonstrated in the Examples below, this screening can be accomplished at the level of a single particle, for example, a single cell, does not require isolation of cells or cellular components from complex mixtures, and does not require large amounts of material for functional screening, produced, for example by immortalizing cells.

Screening methods include both primary binding and secondary functional screening, for example, of a single cell, with an option for recovering the original cell for direct use, immortalization, and/or clonal expansion. The method permits a more complete identification of single cells having a desired functionality early in the development process so that final development of useful biological materials can proceed with a better understanding of the functional characteristics of the molecule and/or cell. Multiple and rapid analyses can be performed on the same single cell, permitting more rapid advancement in the discovery process.

Methods for screening antibodies to identify therapeutic candidates, for example, include depositing one or more particles at one or more location in a microfluidic system, providing the deposited cells with an antibody, and detecting an antibody-induced response in the deposited particles. In an embodiment, multiple particles are deposited at the same location so that the particles are placed in contact or in close proximity with each other, to facilitate functional interactions. Contact or close proximity assures the cells have the ability to react to signals produced and/or bind directly to antigens. In an embodiment, the cells are retained at the location of the deposition that can be a closed microwell, or inverted open microwell system, for example.

In general, analysis of the deposited particle(s) is in a microfluidic system where the particle(s) are held in a stable position within a microwell connected to a micro-sized fluid environment that provides analytical reagents, buffers, and the like, including effective washes and media changes. A single particle, for example a single cell can be deposited, provided with antibody, and monitored for a desired response, such as antigen binding, lysis, or apoptosis induced on a target cell. In an embodiment the deposited particles, for example, one or more cell, are maintained at the location of deposit, on the meniscus at the air/fluid interface of an open microwell, without attachment to a substrate, in the absence of an applied potential or electric field, and without dislodging the single cell from its location.

In a particular embodiment, methods for screening of single particles, including single cells utilize an inverted open microwell system where particles are deposited on an air/fluid interface, or meniscus, of the open microwell. For example, systems such as the inverted open microwell systems described in Bocchi, et al., October 2011, In: *Proc.*

15th International Conference on Miniaturized Systems for Chemistry and Life Sciences, pp. 1722-1724, "Inverted open microwells for analysis and functional sorting of single live cells". Recovery of the deposited particles, for example, a single cell or small aggregate of cells, can be readily performed, for example by pulse pressure release from an open microwell, for example, onto a substrate such as a microtiter plate.

In an embodiment, functional assay of ASC cells includes depositing several particles at a location, including a single ASC, one or more effector cell, and one or more target cell, such that the deposited particles are in contact or in close proximity. Potential lysis of the target cell mediated by antibody secreted by the ASC directly at the site, provides a useful, efficient antibody-dependent cell mediated cytotoxicity (ADCC) assay. In another embodiment, cytotoxic activity of an effector cell against an identified target can be modulated by the presence of a proper antibody, provided to an effector-target cell couple deposited in a microwell, where a potential antibody candidate is provided to the cell couple, for example, in media supplied to the deposited cells and where the effector cell is represented, for example, by a NK cell or a macrophage. Similarly, complement-dependent cytotoxicity (CDC) assays can be performed at the single cell level, where cytoxic activity of an effector cell against a target cell is mediated by complement proteins provided in media supplied to the cells.

In another embodiment, apoptotic activity of an antibody secreted by the ASC directly at the site can be measured, for example, by observing the effect of the antibody on one or multiple target cells. Apoptosis of one or multiple target cells can be detected, for example, with the aid of a fluorescent dye such as Annexin V, or by detecting signaling events rapidly produced in the target cell, such as the flow of calcium which can be observed using a specific fluorescent dye, such as FLUO-4. In another embodiment, the antibody is transmitted through fluid in the microchannel and into the microwell where one or more target cells have been previously loaded.

The deposited particles can include, for example, one or more antibody secreting cell, one or more target antigen, for example located on microbeads or on target cells, and effector cells such as NK cells and macrophages. The antibody can be produced by the deposited ASCs or supplied to the deposited cells from fluid flowing in the device. Additional materials such as nutrients, medium, assay buffer, wash media, proteins, antibodies, chemicals, drugs, growth media and the like can be provided to the deposited cells from the fluid flowing in the device, even in the absence of an electric field.

The deposited particles can include any mixture of specific particles needed to analyze the desired response to the antibody. Antibody secreting cells, effector cells, target particles and cells, and the like can be used. For example, an antibody secreting cell such as a human B cell, can be deposited with a target antigen, that may be bound on one or more microbead, or expressed on the surface of one or more target cell. Antibody binding to a target antigen can be detected by any one of many known methods, for example, using a labeled second antibody, releasing a fluorescent biomarker, and the like. Detection of antibody binding to a desired antigen is a first step in identifying a candidate therapeutic molecule. A second step is directed to identifying a functional characteristic of the antibody.

Functional screening of antibodies or antibody secreting cells can include placing in close proximity an effector cell and target cell, with complement if needed, to determine the ability of an antibody to induce cytotoxicity or cytolysis of a target cell, for example as in an ADCC or CDC assay. The ability of an antibody to induce effector cell cytotoxic or cytolytic activity toward the target cell can identify the antibody as a potential therapeutic candidate.

In an embodiment, the particles and cells are deposited on the air/fluid interface of an open microwell and are stably retained on the meniscus in the absence of a substrate, in the absence of an electric field, and are not dislodged by fluid flow in the microwell. In addition, recovery of the original cell or cells in viable form is possible in the inverted open microwell system.

BRIEF DESCRIPTION OF THE FIGURES

FIG. 1 is a schematic diagram representing the process of primary screening of antibody secreting cells by measuring the binding affinity and selectivity of antibody secreted by a single antibody secreting cell to antigen present on target particles (microbeads or cells).

FIG. 4 is a schematic diagram showing the process of screening antibody secreting cells in an inverted open microwell system when aggregates containing two cells are analyzed. (A) Single ASC cells are isolated in each microwell, (B) particles comprising a target antigen on their surface are added to each microwell in close proximity to the ASC cells, (C) after analysis of the response produced on target particle cells and particles are transferred in standard microtiter plates and (D) monoclonal cell lines are produced in each well of the microtiter plate by clonal expansion of the single antibody secreting cells previously recovered.

FIG. 6 is a schematic diagram depicting a top view of an array of microwells where effector-target cell couples have been delivered and placed at different distances. In (A-C) the location of both the effector and target cell is random, in (D-E) the location of the target cell is controlled by means of forces produced by electromagnetic fields and the cell is positioned at the center of the microwell, while the location of the effector cell is random, in (F) both the effector and target cell position are controlled by means of forces produced by electromagnetic fields and the two cells are positioned at the center of the microwell in contact.

DETAILED DESCRIPTION OF THE PREFERRED EMBODIMENTS

A. Definitions

Figures 2A, 2B, 2C:
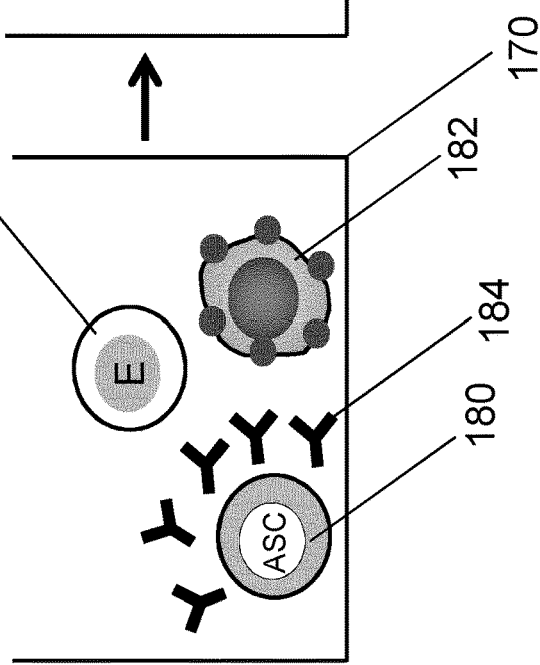
FIG. 2 is a schematic diagram representing the process of functional screening of antibody secreting cells by performing a miniaturized ADCC assay consisting of measuring the cytotoxic effect produced on a effector-target cell pair by antibody secreted by a single antibody secreting cell.

The following terms and phrases are intended to have the definitions shown below:

A means at least one.

Plurality means two or more.

Comprises or comprising means including at least the recited elements or steps, and open to the inclusion of additional elements or steps.

Particle, as used herein, is meant to include any particle that may be delivered, manipulated, reacted, or analyzed in the microwell of the disclosed inverted open microwell system. The particle may be a cell or cellular portion, a microorganism, or a substrate such as a polymeric particle that may be coated with a reactive substance, such as a biological molecule such as a protein, polynucleotide, antibody, enzyme, for example, an antigen coated sphere, and the like.

Antibody-Dependent Cell-Mediated Cytotoxicity (ADCC) is a mechanism of cell-mediated immunity where effector cell of the immune system (NK cell) actively lyses a target cell in a process mediated by specific antibody binding to the target cell.

Natural Killer Cells (NK cell) are cytotoxic lymphocytes that kill target cells by releasing enzymes that induce apoptosis. Action of NK cells is mediated by antibodies specific for the target antigen. Unlike cytotoxic T-lymphocytes, NK cells do not require activation.

Complement Dependent Cytotoxicity is a mechanism for killing tumor cells in which an antibody bound to the target cell surface mediates an attack induced by complement proteins on a target cell and eventually results in lysis of the target cell.

Micro means having at least one dimension less than 1000 micrometers.

Close proximity as used herein, means two or more particles are sufficiently close to each other so as to enable actual reactive contact between particles, such as binding of ligand present on one particle to a receptor present on another particle, or production of a signal by one particle, for example, a cell, that is functionally received by the other cell, for example, binding of antibodies secreted by one cell to an antigen present on another particle; and the like.

Stably retained as used herein, means retained despite fluid flow at the location sufficient to wash and replace buffer at the location.

Meniscus, as used herein, means the air/fluid interface formed at the lower end of the inverted open microwell by surface tension.

Microwell as used herein, means a well formed with micrometer dimensions (less than 1000 micrometers), including height, cross-sectional area, for example, diameter where the microwell is tubular; and volume.

Microchannel as used herein, means a channel providing fluid to the microwell, having a cross-sectional area of micrometer dimensions (less than 1000 micrometers).

Electrode, as used herein, is an electrical conducting material, for example, metal, such as gold, copper, nickel-gold, and the like. Preferred electrodes are formed of high purity gold.

Forces generated by electromagnetic fields, include, for example, dielectrophoresis, electric focusing, magnetic forces, optical tweezers, and the like.

Dielectrophoresis, as used herein, is a force is exerted on a particle when subjected to a non-uniform electric field.

B. Abbreviations

The following abbreviations are used as shown below:
DEP means dielectrophoresis
ASC means antibody secreting cell
NK means natural killer cell
ADCC means antibody-dependent cell-mediated cytotoxicity
CDC means complement-dependent cytotoxicity

C. Methods for Screening Antibody-Secreting Cells

The antibody to be screened can be, for example, a monoclonal antibody, a human or humanized antibody, a chimeric, hybrid, or single chain antibody, The antibody secreting cell can be, for example, transformed cell, hybridoma, immortalized cells, or a hybridoma immortalized with human murine cells, or an immune cell derived from a patient with a specific disease.

Screening of ASC candidates for those producing therapeutically useful antibodies generally involves both primary analysis of antibody binding specificity and affinity, followed by functional analysis of antibody activity, for example, using cytotoxicity assays, such as ADCC, CDC and apoptosis, and detection of cell signaling events, such as intracellular calcium flux. In an embodiment, effector cells, such as NK cells, and macrophages, can be deposited at a location within a microwell together with target cells as deposited cell couples or small aggregates. These groups of cells can be used to screen antibodies for desired therapeutic functions, such as cell lysis or cytotoxicity.

In another embodiment, apoptosis is induced on target cells by the presence of specific antibodies secreted locally by an ASC or delivered to the target cells locally in a fluid containing the antibody. The induction of apoptosis can be detected by known methods, for example, those described in *Apoptosis, Cell Death, and Cell Proliferation*, 3$^{rd}$ *Edition, Roche Applied Science* (roche-applied-science.com/sis/apoptosisidocs/manual_apoptosis.pdf), including fluorescent marker dyes introduced after the antibody has expressed its apoptosis function and by measuring signaling events occurring in target cells, such as intracellular flux of calcium.

1. Primary Screening

Primary screening involves detecting antibody binding to a target antigen that may be expressed on a target cell such as a cancer cell or bound to a target particle, for example, a microbead. With reference to FIG. 1A, in an embodiment, a single ASC 180 is particularly positioned at a specified microwell 170. A target cell or one or more target microbeads 182 are also placed at the specified microwell 170, sequentially or substantially simultaneously. The ASC 180 and target cell or particle(s) 182 can be positioned at a specified position in the microwell by electromagnetic forces, for example creating an electric field between electrodes to manipulate the cell and/or particle(s).

The ASC and target particle are placed in contact or in close proximity at the specified microwell. Each microwell is sufficiently small and sufficiently spaced from other microwells in the system so that diffusion of molecules from one microwell to another is negligible. In one example, ASC and target particle are placed in a central position across a horizontal axis (D-D') of a microwell, such as a central position on the diameter of a microwell having a circular cross-section (FIG. 6F).

Antibody binding to a target antigen can be detected by one of many known methods, including, for example, biomarker identification, binding of secondary antibody or detection of a fluorescence, optical, or impedance signal, for example.

Screening of an ASC in an inverted open microwell system can also include determination of the produced antibody's specificity for the target antigen. For example, by introducing into the microwell increasing concentrations of particles comprising non-target antigens, specific binding of the antibody to the target antigen can be measured. Generally, an antibody having low specificity will be blocked from binding the target antigen by the presence of non-target antigens at a lower concentration of non-target antigen than a the concentration required to block the binding of a specific antibody.

2. Primary Screening Procedure in the Inverted Open Microwell System

With reference to FIG. 4, an exemplary procedure for primary screening using an inverted open microwell 102 or an array thereof 100 is outlined below:

1) An ASC population is prepared by collecting cells that may be mouse or human B cells, for example obtained from a patient likely to have a substantial number of B cells of interest or any other ASC prior to immortalization, or B cells that have been immortalized, for example, by EBV or fusion or electrofusion or any other suitable procedure; or hybridoma cells previously produced by fusing mouse or transgenic mouse spleen cells with myeloma cells, according to methods known in the common practice.

2) Microbeads are prepared by binding a specific target, such as an antigen or protein, or a secondary antibody specific to mouse or human IgG on their surface. Alternatively, target cells, such as tumor cells, expressing a specific epitope on their membrane can be used.

3) A fluid containing microbeads or target cells 128 is inserted in the microchannel and single particles are delivered to each inverted open microwell (FIG. 4A)

4) A fluid containing ASC is inserted in the microchannel and single ASC are delivered to each inverted open microwell and placed in close proximity or in contact to target cells or microbeads (FIG. 4B)

5) Object pairs are kept in each microwell at the interface between air and fluid for a time suitable for properly binding the antibody secreted by the ASC to the microbead or the target cell. This time typically ranges from 30 minutes to 3 hours.

6) Filtered air or a mix of air and CO2 can be flowed in the channel, removing the fluid from the channel while retaining fluid in the microwells. Saturated humidity conditions can be preserved both in the channel and outside the device to avoid fluid evaporation from the microwells. In this configuration, antibody concentration reaches much higher values because of the small volume of fluid.

7) Object pairs are kept in each microwell at the interface between air and fluid for a time suitable for properly binding the antibody secreted by the ASC to the microbead or the target cell.

8) Physiological buffer is returned to flow in the channel, restoring initial fluidic conditions.

9) A fluid containing fluorescence labeled secondary antibody specific to mouse or human IgG is flowed in the channel, replacing the fluid around the microbead or target cell and allowing the secondary antibody to bind to the target.

Figure 3:
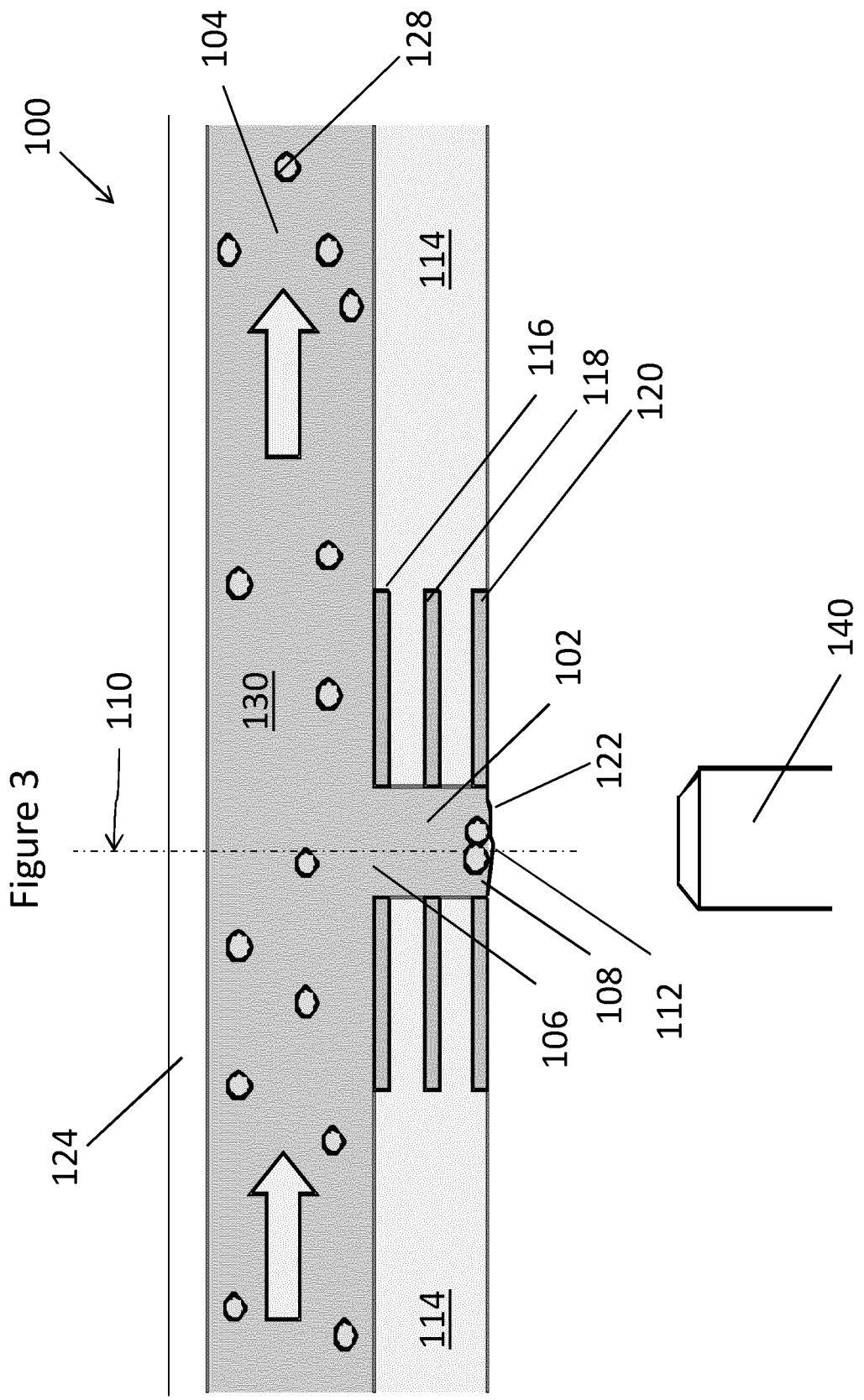
FIG. 3 is a cross sectional diagram showing the isolation of cell aggregates in an inverted open microwell system having a 3 electrode configuration.

10) Using an inverted microscope 140 depicted in FIG. 3, each well is monitored from the bottom side under fluorescence. A fluorescent signal emitted from the microbead corresponds to the proper binding of the antibody to the target. The intensity of the fluorescent signal emitted by the single microbead increases with the antibody affinity.

11) The content of each microwell is transferred to an external microwell of a microtiter plate (FIG. 4C).

12) If the recovered cell were immortalized prior to the screening process, cell growth will be possible and after some days each microwell will contain a monoclonal line of ASC. Alternatively, antibody cDNA can be recovered and amplified from the single cell, analyzed and transfected to immortalized cells, such as CHO cells.

3. Detection of Antibody Binding

Binding of the antibody to the target cell or particle(s) can be detected by known methods, for example by detection of a marker present on the target antigen, by a secondary antibody, by release of a fluorescent color, or impedance signal, and the like. For example, binding of secreted antibody to the antigen can be observed by adding a fluorescence-labeled secondary antibody 186 to the surrounding medium, and observing the fluorescent signal (FIG. 1C). To increase the signal to noise ratio, the ASC can be cultured in serum-free medium, and the assay also conducted serum free.

Antibody binding to the target particle (for example, target cell or antigen) can be detected using any suitable method, such as by biomarkers, measuring, for example, chemical, fluorescent, optic, or colorimetric signals, and the like, as a measure of antibody/antigen binding. In a particular embodiment, the binding is measured by means of an inverted microscope 140 under fluorescence or by a custom imaging system positioned to observe the microwells, for example, under an inverted open microwell array. Biomarkers and tags can be incorporated into the antigen or a secondary antibody, such as anti-IgG. For example, when a fluorescence-anti-IgG is used as a marker, the presence and intensity of emitted fluorescence correlates with the amount of antibody binding.

4. Secondary, Functional Screening of ASC

The output of the primary screening process identifies cells with a desired affinity and specificity towards a target antigen. This primary screening can be followed by secondary functional screening of ASC identified as having the desired binding characteristics. During secondary screening, secreted antibody function is analyzed, for example, by detecting the effect of the secreted antibody on target cells.

A work by R. Bhat and C. Watzl, entitled "Serial Killing of Tumor Cells by Human Natural Killer Cells—Enhancement by Therapeutic Antibodies", *PLoS ONE,* 2007, 2(3):

e326, represents one study of the efficacy of a therapeutic antibody in boosting NK cells activity against 221 tumor cells. Like this study, the methods currently available for ADCC analysis only allow performance on large cellular aggregates, without any control on the single cell. Consequently, this approach does not provide any means to test antibodies directly secreted by the ASC.

The present invention teaches how to perform the secondary screening of a monoclonal antibody by performing the ADCC assays on target-effector cell couples, where the tested antibody is added to the surrounding medium, or where the antibody is secreted locally by the presence of an ASC. In one embodiment of the present invention, the ADCC assay is performed by creating couples or aggregates including a NK cell and a target 221 cell, where the cytotoxicity is mediated by an anti-CD20 antibody, such as the Rituximab produced by Biogen Idec, or where the NK cytotoxic activity is boosted by molecules such as the IL-2 added to the culture medium.

In an embodiment, a selected ASC can be contacted with a target cell expected to be selectively opsonized by the produced antibody, for example, a tumor cell. Phagocytosis of the target cell by a phagocyte cell deposited in the microwell and in close proximity with the target cell and antibody producing cell, for example, where the phagocyte is a macrophage, eosinophil, or neutrophil, confirms a utility of the antibody and the ASC.

In another embodiment, functional assay is by Antibody-Dependent Cell Cytotoxicity (ADCC) assay, involving specific reactions between the antibody secreted by the ASC, a target cell expressing antigen, and an effector cell. With reference to FIG. 2A, a cluster of these three cells is deposited at a location in a microwell, where each cell is in contact or close proximity to the others. Antibody secreted by the ASC (or provided to the deposited cells when the ASC is absent) binds to antigen present on the target cell (FIG. 2B), and the effector cell induces lysis of the target cell (FIG. 2C).

In another embodiment, functional assay is by Complement-Dependent Cytotoxicity (CDC) assay, involving specific reactions between antibody provided to the deposited cells or secreted by the ASC, a target cell expressing antigen, and complement proteins. A cluster of the two cells is deposited at a location in the microwell, with the two cells in contact or close proximity. After antibody secreted by the ASC (or provided to the deposited cells) binds to antigen present on the target cell, complement proteins are provided to the deposited cells in the fluid medium, and eventually induce lysis of the target cell.

In another embodiment, functional assay is by apoptosis assay, involving specific reactions between antibody provided to the deposited cells or secreted by the ASC and a target cell expressing antigen. A cluster of the two cells is deposited at a location in the microwell, with the two cells in contact or close proximity. After antibody secreted by the ASC (or provided to the deposited cells) binds to antigen present on the target cell, it induces apoptosis of the target cell, which can be determined by known methods. The proper binding and functional activity on the target cell can also be determined by a signaling event on the target cell, for example, the intracellular flux of calcium.

In the ADCC and CDC assays, after confirming lysis of the intended target, the selected ASC can be immortalized, expanded, and/or recovered from the microwell for therapeutic and diagnostic development.

5. Secondary, Functional Screening of Monoclonal Antibodies in Fluid Form

In the common practice, ADCC assays provide information about a specific antibody collected from the supernatant of ASC cultures. Known assays make use of a large number of target and effector cells properly mixed with a controlled effector:target ratio. Cytotoxicity is typically measured on average and correlated to the presence of a monoclonal antibody or other molecules boosting the activity of effector cells, for example, IL-2 used as promoter of NK cell activity. Existing methods fail in providing a controlled positioning of the effector and target cells and do not allow any precise control of the number of target and effector cells composing the aggregate. Moreover, the effect of the distance among effector and target cells is difficult to be characterized.

In an embodiment, this invention teaches how to position a controlled number of effector cells and a controlled number of target cells in each microwell. Using an array of microwell, for example, inverted open microwells, a controlled number of cells can be isolated in each microwell by repeating the delivery procedure represented in FIG. 4A. As a result, deterministic number of effector and target cells can be isolated in each microwell. With reference to FIG. 3, after the formation of cellular aggregates, a fluid containing a monoclonal antibody is inserted in the microchannel and the antibody reaches each microwell by diffusion and/or fluid exchange. The functional effect of the antibody can be measured in each microwell and correlated to the effector:target ratio created in each microwell. The result of multiple ADCC assays executed in parallel on multiple microwells provides a characterization of the antibody function correlated to the effector:target ratio.

In another embodiment, the ADCC assay is executed on effector-target cell couples isolated in inverted open microwells where the distance between the effector and the target cell is controlled by means of electric fields. With reference to FIG. 6, in the case A, B and C the target cell 182 and the effector cell 188 are delivered to a microwell without any electromagnetic field activated. The location of the two cells is random and the distance between the two cells varies to a maximum corresponding to the microwell diameter, for example, 80 micron. In the case D and E, the target cell 182 is positioned at the center of the well by activating the electromagnetic field during the delivery procedure, while the effector cell 188 is randomly deposited in the microwell, as the electromagnetic field is deactivated during the delivery procedure. The resulting distance varies to a maximum corresponding to about half the diameter of the microwell, for example 40 micron. In the case F, both the target and effector cell are delivered while keeping the electromagnetic field active and result to be in contact with a distance of about 0 micron. After the delivery phase, the actual distance in each microwell is determined by fluorescence imaging and by processing the acquired images. Then a monoclonal antibody is added to each microwell and the cytotoxic effect of the effector cell on the target is measured by monitoring the lysis of the target cell. The method eventually provides information about the function of the monoclonal antibody correlated to the distance of the different effector-target cell couples analyzed.

6. Functional Screening of ASC in an Inverted Open Microwell System

The inverted microwell system provides efficient and effective real-time monitoring of particle functions, including interactions of multiple particles, functional screening and sorting of particles, for example live cells. In a particular embodiment, the system provides high throughput functional analysis of antibody secreting cells, analysis of lytic activity of cytotoxic and natural killer cells, for example by ADCC or CDC assay at the single cell level. The system also permits measurement of the affinity and specificity of molecules secreted by single cells, for example, monoclonal antibodies.

Other methods include the screening of antibody secreting cells (ASC) at an early stage by depositing a single antibody secreting cell, for example, and early B cell, onto the meniscus of an inverted open microwell. Following binding specificity and affinity analysis of antibody secreted by the deposited ASC, those cells selected as secreting antibodies with suitable binding activities can be rapidly screened, for example, in the same open microwell, for the ability to induce cytotoxic activity against a target cell as modulated by the produced antibody, for example, in ADCC and/or CDC assays at the single cell level. A selected ASC can be clonally expanded within the open microwell, or optionally the selected ASC can be recovered from the microwell and expanded in other systems. In a similar manner, antibodies produced from the ASC can be recovered from the single cell production, for example, bound to antigen-coated microbeads, or collected as produced from expanded cells in the culture. Expanded cells and/or secreted protein can be isolated and used to determine antibody gene and/or protein sequence, for example, for use in the production of engineered antibodies, fragments, or other therapeutic molecules.

With reference to FIG. 4, in an embodiment the secondary screening process is performed within an inverted open microwell 102 or an array thereof 100. The procedure for the secondary functional screening can be, for example, based on the following steps:

1) An ASC population is prepared by collecting cells that may be mouse or human B cells, for example obtained from a patient likely to have a substantial number of B cells of interest or any other ASC prior to immortalization, or B cells that have been immortalized, for example, by EBV or fusion or electrofusion or any other suitable procedure; or hybridoma cells previously produced by fusing mouse or transgenic mouse spleen cells with myeloma cells, according to methods known in the common practice.

2) Using the inverted open microwell system, different cell types are inserted in the microchannel (FIG. 4A) and individual cells are deposited in the open microwell, forming clusters of cells in contact or in close proximity in the microwell (FIG. 4B). Each cluster can include an ASC to be screened for functional properties of the produced antibody, target cells that should be selectively opsonized by the antibody produced by the ASC in the same cluster, and effector cells able to induce lysis in cells suitably opsonized (ADCC assay); alternatively, lysis could be induced by complement proteins (CDC assay); alternatively, apoptosis is induced on the target cell by the antibody bound to one antigen expressed by the target cell.

3) Observation with fluorescence microscopy is carried out at each microwell to verify the occurrence of lysis or apoptosis induced by the effector cell or protein or antibody on the target cell and possibly mediated by the presence of the antibody secreted by the single ASC.

4) Recovery of the ASC cells onto a microtiter plate is performed and information about the functional properties of the secreted antibody is recorded and associated to each ASC recovered (FIG. 4C).

5) ASC identified in the binding and/or functional assay as having desirable qualities can be cultured and expanded in the microtiter plate to form monoclonal cell lines (FIG. 4D).

Cell lines of interest for the specific disease can be selected on the basis of the information gathered during the screening procedures.

7. Particle Delivery to Microwells

In an inverted open microwell system as shown in FIG. 3, ASC and target particle are transported within a microchannel 104 and into a microwell 102 by one or more of limiting dilution, fluid flow, and sedimentation, electromagnetic forces, such as dielectrophoretic forces, and gravity. In particular, the ASC and target particle are placed at a central location of a meniscus 122 formed at the air/fluid interface of the lower end of an inverted microwell. If an electromagnetic field is activated in the microwell during the descent of two particles to the meniscus, an aggregate 112 is formed, placing the particles in contact or in close proximity. Deposition of the ASC and target particle on the meniscus can be substantially simultaneous or in sequential order.

Such proximity of the ASC and target particle, combined with limited size of the microwell, ensures that antibody 184 secreted by the ASC reaches the antigen for potential binding (FIG. 1B).

8. Recovery of Antibody

Bound antibody can be recovered from the target particles(s), for example, on release of surface tension at the meniscus permitting cells and fluid in the microwell to be transferred to a substrate beneath the microwell, for example, a microtiter plate. The recovered antibody can be used for further antibody development. In an embodiment, analysis of the secreted antibody protein and/or analysis of the recovered ASC DNA can be used to develop and identify probes and otherwise serve to aid production of synthetic humanized antibodies and fragments.

9. Recovery of Deposited Cell or Cells

After an ASC is identified as capable of producing a specific and/or functional antibody, the ASC can be recovered from the microwell and used to produce a monoclonal cell line. When a closed microwell is used, cell recovery can be performed with a micromanipulator, for example, positioning a micropipette and aspiring the content of a single microwell and then ejecting the liquid and the cells into a destination receptacle, for example, a well of a standard microtiter plate.

Figure 9:
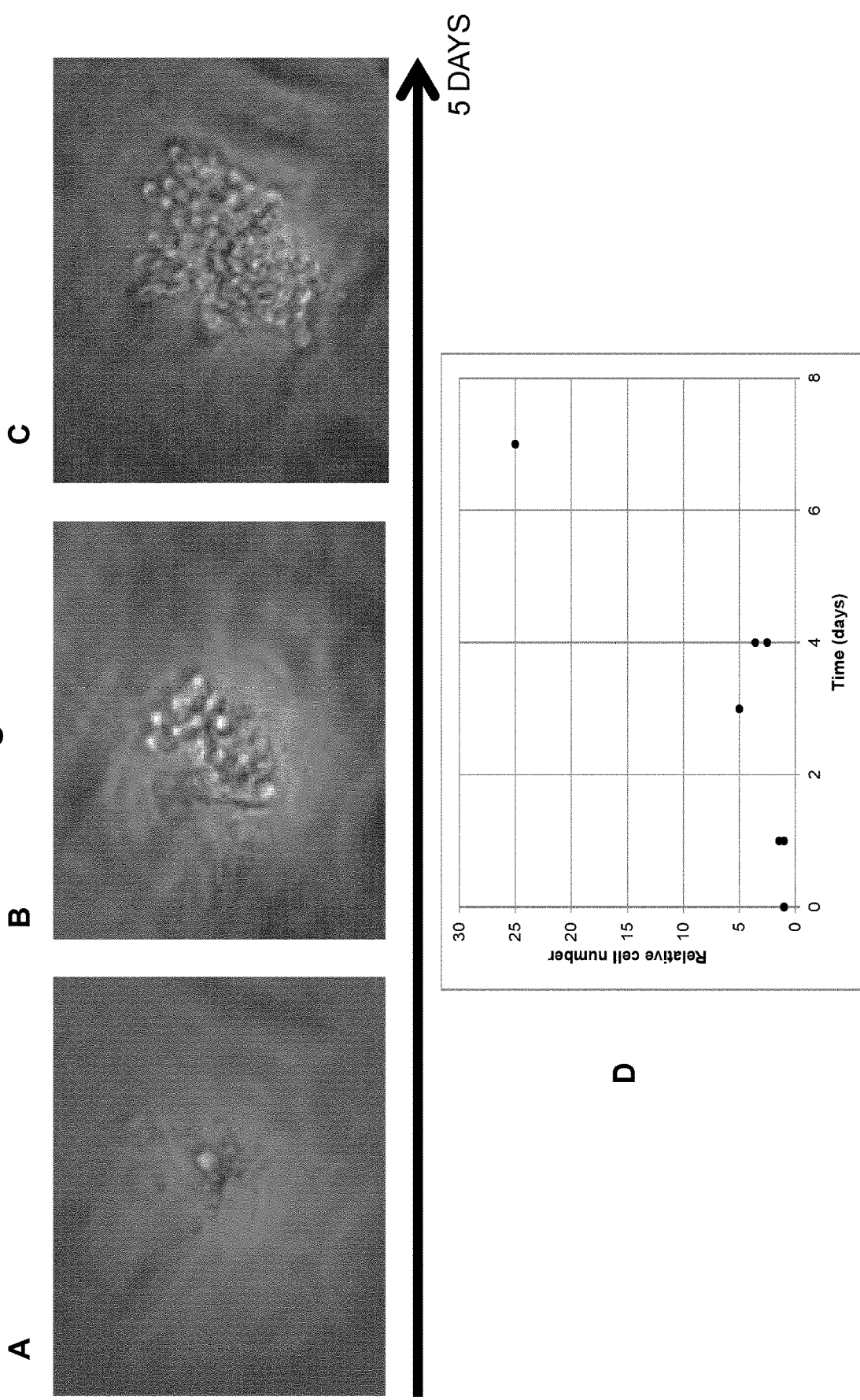
FIG. 9 is a series of photographs demonstrating clonal expansion of a single K562 cell recovered from an inverted open microwell and transferred to V-shaped microtiter plates for expansion over 5 days: A=day 0; B=3 days; 0=5 days. A graph showing rapid increase in the relative number of cells over seven days is also shown (D).

When an inverted open microwell system is used, for example, the contents of the open microwell can be released into a vessel or onto a substrate, for example by applying a short burst of pressure in the microchannel sufficient to disrupt the meniscus and drop the contents of the microwell into a vessel or substrate, for example, a microtiter plate. The recovered cell can be clonally expanded outside the microwell (FIG. 9). Alternatively, expansion of the single cell ASC can occur within the microwell itself.

Importantly, in the inverted open microwell method and system as described, the deposited cell or cells, for example, an antibody secreting cell, can be recovered from the microwell in viable form. In one embodiment, a pressure pulse is applied to the microchannel, causing droplets to be released from the microwell from the bottom of the open microwell and to a capture surface, for example a microtiter plate. The recovered ASC can be immortalized, with clonal expansion of the single recovered ASC. The produced monoclonal cell line secretes a monoclonal antibody with affinity and specificity initially measured at the single cell level. Growth of a cell line from a single cell recovered from an inverted open microwell system is represented in FIG. 9.

D. Apparatus for Screening Antibody-Secreting Cells

1. General Characteristics of Microwells for ASC Screening

Screening of cells performed on the basis of their ability to secrete molecules of interest requires the design of proper microwells where the screening process takes place. Two main requirements for said microwells are: (i) the need of achieving a sufficiently high concentration of the molecules of interest in a short amount of time and (ii) the need of minimizing or eliminating the diffusion of molecules from one site to the adjacent ones.

The first requirement directly impacts the sensitivity of the measurement method. Two techniques can be combined to optimize the overall sensitivity. The first one is a reduction of the microwell volume, so that the concentration of the secreted molecules can achieve high values in a time compatible with other experimental constraints, for example, from minutes up to a few hours. U.S. Pat. No. 7,776,553 teaches that by using microwells closed on both top and bottom sides with a volume of 10 nL or less it is possible to reach detectable concentration of antibodies secreted by single cells in a matter of 4-8 hours. A work by J. L. Ronan et al. entitled "Optimization of the surfaces used to capture antibodies from single hybridomas reduces the time required for microengraving", *J. Immunol. Methods*, January 2009, 340(2), pp. 164-169, teaches how to reduce the screening time down to 3-10 minutes by optimizing capture surfaces.

A second strategy to increase the amount of captured molecules is to place the secreting cell in close proximity to the detection surface. In fact the flux of secreted molecules increases when reducing the distance to the source. This methodology is commonly adopted in the ELISPOT® assay, where fluorescent spots are produced on a substrate as a result of the secretion of molecules by cells. These spots are produced around the cell, demonstrating that even in a large volume the local concentration of secreted molecules can still be high enough to be detectable.

Another work by A. Jin et al. entitled "A rapid and efficient single-cell manipulation method for screening antigen-specific antibody-secreting cells from human peripheral blood", *Nature Medicine*, 2009, 15, pp. 1088-1092, teaches that antibody secreted by B lymphocytes can be detected locally by isolating single cells into microwells with a closed bottom side having a diameter of 10 µm and a height of 15 µm, even without closing the top side of the microwell. In this case the detection is executed by observing the binding of the secreted molecules onto the surface surrounding each microwell. This work also teaches that a pitch of 20 µm between the microwells is high enough to limit the interference of the signal produced from one microwell into the adjacent one.

The present invention makes use of microwells having characteristic sizes comparable to the ones previously described. In some embodiments the microwell, either open or closed at the lower end, has a diameter of 100 µm or less and height included between 25 µm and 150 µm. The present invention also exploits the proximity of the ASC to the measurement region, in order to obtain even higher sensitivity of the measurement. The object of the measurement is intended to be either the binding of the secreted antibody to a target antigen or the ability of the secreted antibody to mediate the cytotoxic activity of an effector cell on a target cell. When the measurement takes place in a microwell, the ASC and the other particle(s) used to perform the measurement are placed on the bottom side of the microwell, while a microchannel connecting the different microwells is on the top side. In these conditions, by increasing the height of the microwell it is possible to increase the distance between the ASC and the microchannel and consequently reduce the interference of each ASC on the other ASCs isolated in adjacent microwells.

In one embodiment the detection of antibody affinity and specificity is performed by placing a microbead coated with a target antigen or a target cell including a target antigen on its surface in close proximity or in contact with the ASC, by means of forces generated by electromagnetic fields, for example, dielectrophoresis.

In a different embodiment, the functionality of the secreted antibody is determined by observing the cytotoxicity of a NK cell against a target tumor cell, where the NK cell, the target cell and the ASC form an aggregate where the three cells are in contact or in close proximity, i.e. have a distance of 20 µm or less.

2. Use of the Inverted Open Microwell

The process of screening antibody secreting cells is improved as described herein, by performing functional screening upstream of the immortalization of antibody secreting cells, for example, by screening secreted antibodies for functional activities at the level of single ASC. Such screening on a single cell level enables the antibody function to be assessed rapidly, for example, in only a few days, and is easily performed on a large number of candidates. In one embodiment, primary screening of antibody binding, affinity and selectivity can be performed on the same cell and in the same microfluidic system as secondary screening of antibody function, producing a complete characterization in a matter of days. In another embodiment, the discovery of new therapeutic human antibodies with highly specific activity against target antigens and demonstrated functional therapeutic activity is achieved by means of using the unique properties of the inverted open microwell system.

Delivery of single cells to microwells, precise manipulation of cells and other particles in the microchannel and into or away from a specific microwell, delivery of reagents, buffers, markers and the like, including other cells for cell-cell interactions, is facilitated by the inverted open microwell system shown in FIG. 3. Single cells can be evaluated for multiple characteristics, retaining vitality in the open microwell for optional expansion and recovery of the particles and of products produced by the particles is possible in a short time frame, using minimal reactants, and recovering cells and products in a substantially viable and useful condition.

In particular, deposition of one or more particles, including live cells, at the fluid/air interface of an open microwell permits precise particle to particle interactions that can be efficiently monitored and rapidly screened to identify candidate particles, for example cells, for continued analysis in the microwell. Surprisingly, the fluid filling the microwell featuring an open lower end is retained in the microwell without leakage, when proper geometrical constraints and fluidic conditions are ensured. Moreover, the deposited particle(s) are surprisingly retained at the meniscus during fluid washes and analytical procedures, and can be recovered in viable form.

Figure 5B:
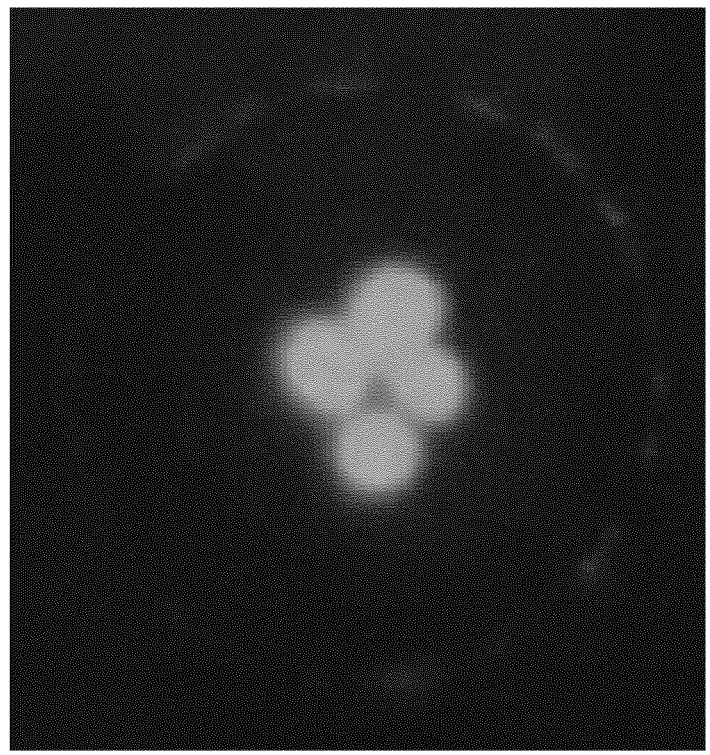
FIG. 5 is a set of photographs of K562 cells observed with an inverted fluorescence microscope after deposition on the meniscus of an inverted open microwell, where (A) K562 cells were deposited randomly in the absence of an electric field and (B) K562 cells deposited in an aggregate near the center of the meniscus when electromagnetic forces focused the particles to a central position in the microwell during vertical descent and deposition of the cells.
Figure 5A:
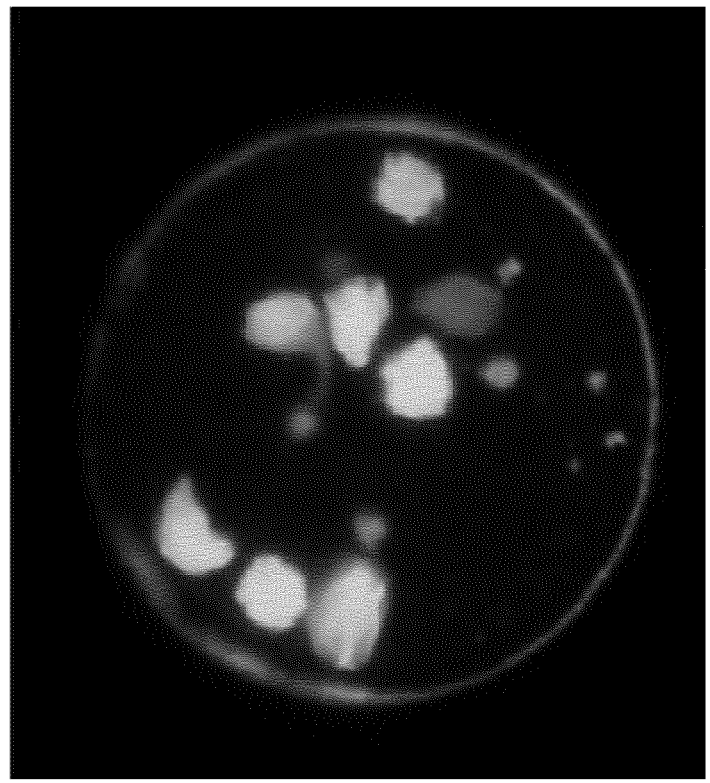

The open microwell acts as a "mini-centrifuge" permitting rapid analysis, washes, delivery of fresh reagents, and continued analysis of the deposited particle. When multiple particle are delivered to the same microwell, being them of the same type or different type, the open microwell system allows the creation of cell aggregates where the cells are placed in contact each other by activating electromagnetic fields which produce dielectrophoretic forces within the microwell. FIG. 5B show the effect of the activation of electromagnetic field in creating the cell aggregate, while FIG. 5A, shows the effect of cell delivery in an inverted open microwell where the electromagnetic field has not been activated.

Recovery of the contents of the open microwell, including viable cells identified as useful, is possible, for example, as shown in FIG. 4C. Pressure applied to the fluid microchannel can be used to disrupt the meniscus at the lower end of the inverted open microwell and discharge the contents of the microwell onto a substrate, for example, a microtiter plate, array of micro-vials, and the like.

The present invention is further described by way of specific examples, which are intended only as exemplary embodiments, and are not intended to limit the scope if the invention in any way.

EXAMPLES

Example 1. Binding of Anti-P53 Antibody to Antigen-Coated Microbeads

The purpose of this experiment was to demonstrate a protocol to perform the analysis of antibody secretion by hybridoma cells using polystyrene microbeads as the binding surface. To prove the effectiveness of this method, we suspended p53-coated microbeads with hybridoma cells after having changed the hybridoma supernatant with fresh medium to remove antibodies previously secreted during cell culture. The binding of anti-p53 antibody secreted by hybridoma cells to the microbeads in close proximity was demonstrated.

Coating of Beads. Polystyrene microbeads having a diameter of 10 μm were suspended in a concentration of 106 beads/mL in borate buffer (0.1M boric acid adjusted to pH 8.5 with 1M NaOH). Microbeads were washed twice in borate buffer and resuspended in 100 μL of borate buffer containing p53 protein in a concentration of 4 μg/mL. The bead suspension was then plated in 4 microwells (25 μL per well) of a 96-well microtiter with U-bottom wells, in order to obtain a single layer of microbeads on the bottom of the well. After overnight incubation, the protein solution was removed and the microbeads were resuspended twice for 30 min at room temperature in 200 μL of blocking solution (10 mg/mL bovine serum albumin in borate buffer). Finally, the microbeads were washed twice in PBS.

Antibody binding and screening. Mouse hybridoma cells PAb1620 (DSMZ) producing monoclonal antibodies to p53 wild-type protein were centrifuged at 1500 rcf for 5 minutes and resuspended in fresh Dulbecco's Modified Eagle Medium (DMEM) to a final concentration of $1.3 \times 10^6$ cells/mL. Polystyrene beads coated with p53 protein were centrifuged and resuspended with cells. Several wells of a 96 well microtiter plate were filled with 200 μL of the suspension containing beads and cells and incubated at room temperature with gentle mixing. As negative control, the suspension containing only p53-coated microbeads was plated on a certain number of wells without being mixed with hybridoma cells. As positive control, the suspension containing p53-coated microbeads was plated to a certain number of wells and a primary anti-p53 antibody was added in a concentration of 15 μg/mL.

After 3 hours the plate was centrifuged at 700 rpm for 2 minutes, the supernatant was removed and 200 μL of anti-mouse secondary antibody (1:200 in PBS-Tween) was added. After 3 hours incubation at room temperature with gentle mixing, the plate was centrifuged for 2 minutes at 700 rcf and each well was washed twice with PBS. The binding to the microbead was detected using an inverted microscope with a FITC filter. Fluorescence on microbeads was detected and fluorescence intensity extracted with single-bead resolution.

The average intensity measured on several images acquired is reported in Table 1. Antibody secreted by hybridoma cells produced a fluorescent signal consistently higher than negative control. Also, comparing to positive control we obtained a 33% higher intensity for hybridoma cells, suggesting that the equivalent concentration of secreted antibody was higher than the control case. The result of this experiment demonstrates binding of an antibody secreted by antibody secreting cells to the surface of microbeads properly coated with a desired target antigen, where the ASC and microbead particles are in close proximity.

TABLE 1

Results of antibody binding to p53-coated polystyrene microbeads

| Experiment | Average fluorescence Intensity | Sample # |
|---|---|---|
| PAb1620 hybridoma | 33.80 | 39 |
| Positive control (anti-p53mAb) | 25.32 | 31 |
| Negative control (no mAb) | 3.34 | 8 |

Example 2

Binding of Antibody Secreted by Murine Hybridoma to Cell Surface Antigen

The purpose of this experiment was to demonstrate a protocol to perform the analysis of antibody secretion by hybridoma cells and binding of the secreted antibodies to surface antigens on melanoma target cells. To prove the effectiveness of this method, melanoma cells were suspended with hybridoma cells. The hybridoma cells secreted a murine monoclonal antibody capable of reacting with molecules displaying the typical molecular profile of class II MHC antigens. Binding of the secreted antibody to target cells was demonstrated using a hybridoma concentration that is comparable to the equivalent concentration of one cell in a 100 μm microwell in an array of microwells having a 2.25 mm pitch.

Mouse hybridoma cells were stained with MitoTracker® fluorescent dye (20 nM in PBS for 20 minutes) and resuspended in RPMI+10% FCS. The cell suspension was diluted to $5 \times 10^4$ cells/mL and 50 μL of this suspension were deposited into wells of a 96-well clear flat bottom microtiter. 50 μL of target melanoma cells suspended in RPMI+10% FCS at the same concentration were added to the suspension. The co-culture was incubated at room temperature for 30 minutes, then the suspension was washed twice with 100 μL PBS (centrifuge 700 rpm, 2 minutes), the supernatant was removed and 200 μL of anti-mouse secondary antibody (1:200 in PBS-Tween) was added. As negative control, the secondary antibody was added to a cell suspension containing only target melanoma cells.

Figure 8:
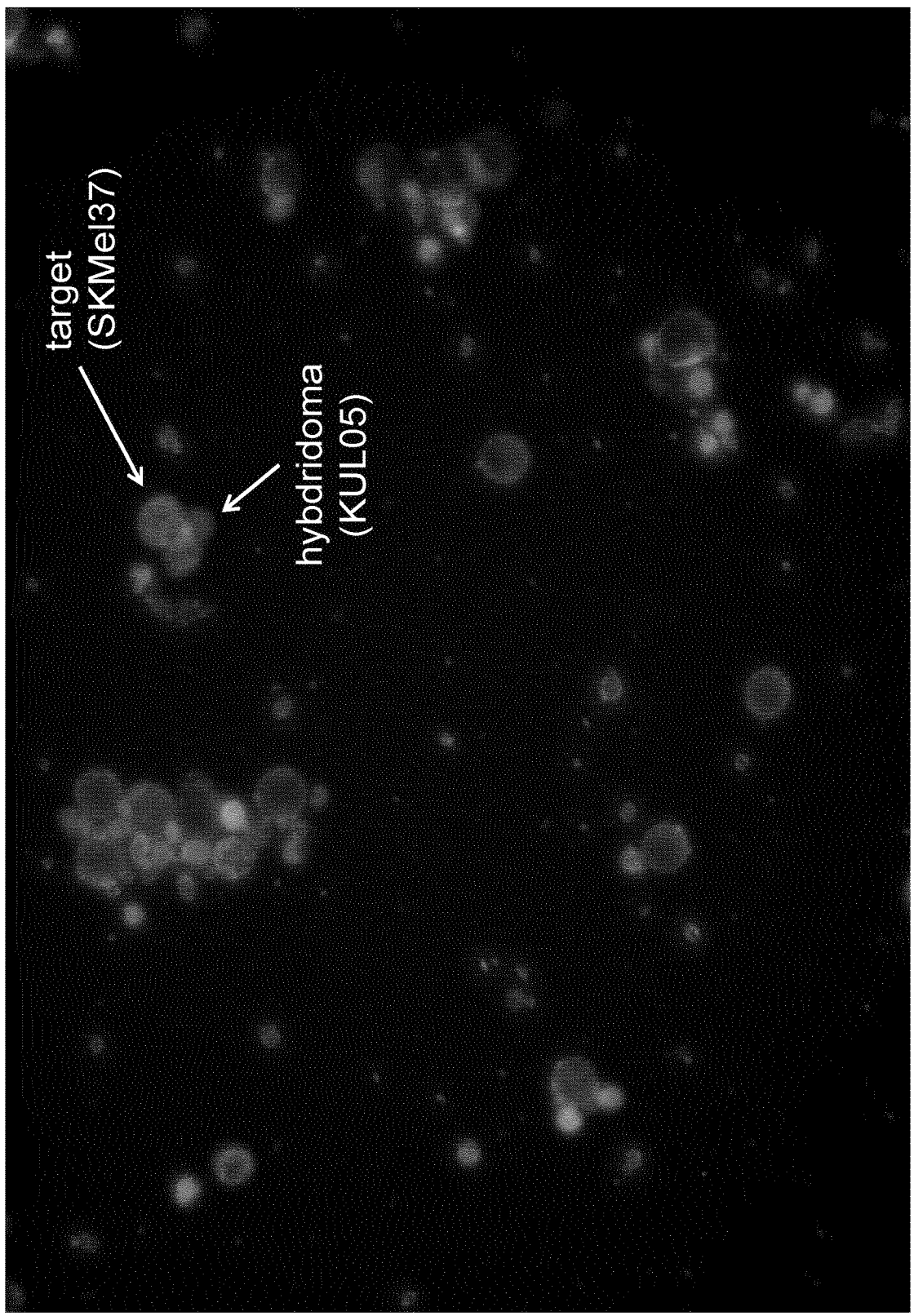
FIG. 8 is a photograph of KUL05 hybridoma cells marked with a red fluorescent dye (MitoTracker®) incubated with target SKMe137 melanoma cells expressing a target antigen on the cell surface. After the addition of a fluorescent secondary antibody (anti-mouse) the target cell are visible under green fluorescence, demonstrating the binding of the secreted antibody, and can be distinguished by hybridoma cells which appear both red and green under fluorescence lighting.

After 30 minutes cells were washed twice with 100 μL PBS and resuspended in 100 μL PBS. The binding to target cells was detected using an inverted microscope with FITC/TRITC filters. All cells were visible under green fluorescence (FITC). Using the red fluorescence (TRITC filter) and analyzing cell shape, target cells were distinguished from hybridoma cells. Green fluorescent signal was clearly visible on target cells and was not detectable in the negative control. FIG. 8 shows a photograph obtained under fluorescence imaging at the end of the process. From the figure, target cells appear as green round spots and can be easily distinguished from hybridoma cells appearing as red spots. The appearance of the green fluorescence on target cell demonstrates the binding of secreted antibodies to target cells is possible within one hour, where the binding of the secreted antibody to the target cells was performed within the first 30 minutes of incubation, and the binding of the secondary fluorescent antibody was performed in other 30 minutes.

Example 3

Activity of NK Cells Against Target 221 Cells

Analysis of cell-cell interactions at the level of small cell aggregates, sometimes comprising a single target tumor cells was demonstrated in this experiment. The biological system used in this experiment is represented by 221 cells as target cells and by NK and YTS cells working as effector cells. This system has been widely studied with the purpose to understand the immunological mechanisms at the basis of cell-cell interactions and to measure the functional effect of therapeutic monoclonal antibodies in activating the activity of the effector against the target cell. The work of R. Bhat and C. Watzl cited above in this document is an example of the studies conducted on this system.

In the experiment here described the inverted open microwell system was used to isolate the cell aggregates and to monitor the interactions. All cells were cultivated in flasks at 37° C. and 5% CO2 in RPMI medium and for NKL with addition of IL-2. Target cells were marked with calcein and suspended in NaCl 0.9% sterile solution. NK cells (NKL and YTS) were washed and re-suspended cells in NaCl 0.9% sterile solution. Target cells were inserted in the microchannel of the inverted open microwell system at a flow rate of 8 µL/min and delivered to the microwells with a diameter of 70 µm as to have 1 or 2 cells per microwell. Effector cells were then inserted in the same conditions and delivered to the same microwells in order to have about 1-5 effector cells per microwell. Control experiments were executed by delivering only target cells into a few microwells. A continuous flow of NaCl 0.9% was maintained in the microchannel while monitoring the fluorescence intensity produced by the calcein-marked cells.

Figure 7:
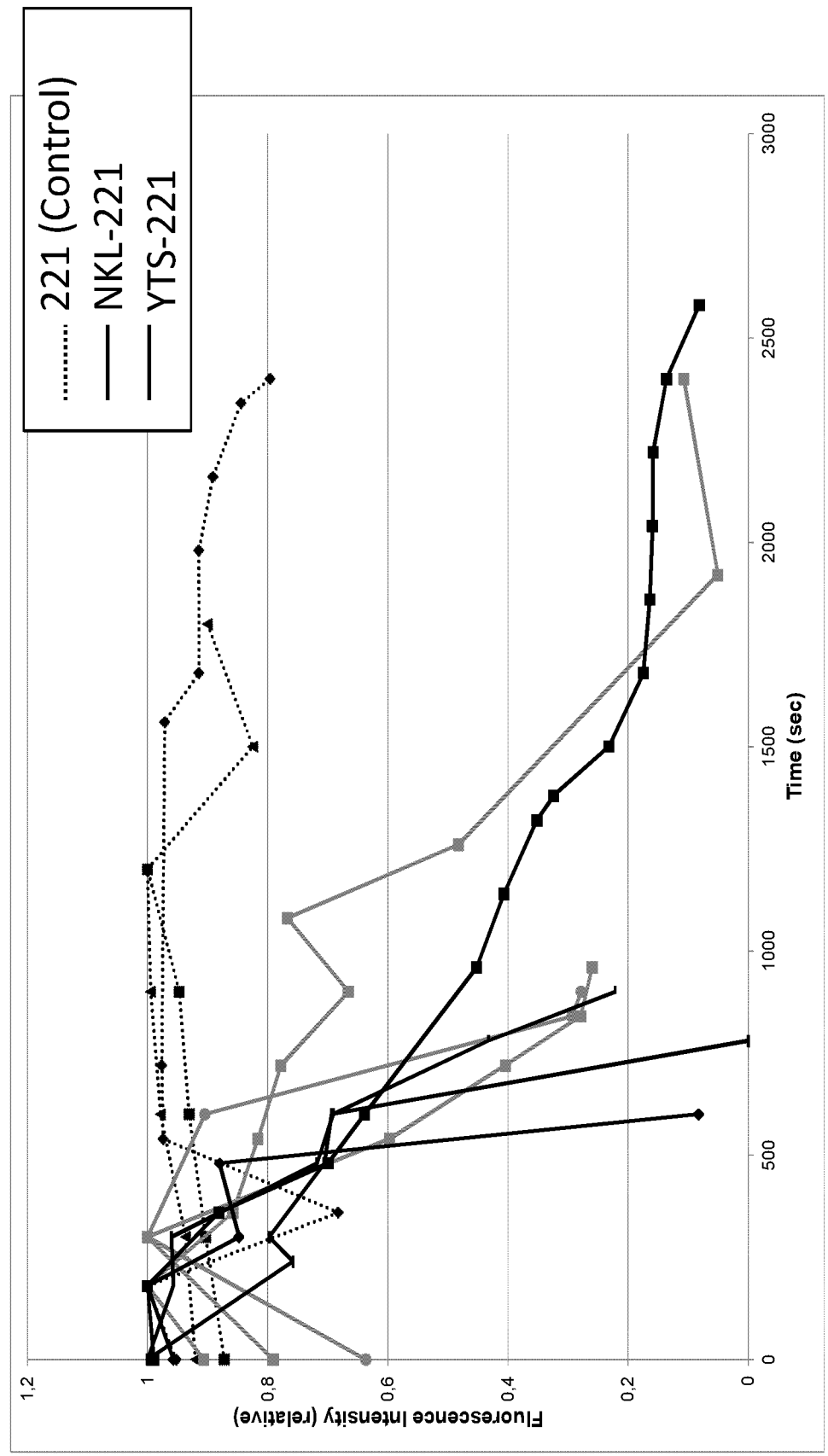
FIG. 7 shows the fluorescent signal emitted by target cells marked with calcein in an experiment where single 221 target cells were isolated with NKL and YTS effector cells into an inverted open microwell and monitored. The decrease in fluorescent signal demonstrates the lysis of target cells induced by the effector cells, whereas control experiments show only a minimal physiological decrease of the fluorescent signal.

The observation lasted for a maximum of 30 minutes. This time was sufficient to achieve the lysis of all target cells exposed to the effector cells. The fluorescent signal of single target cells was recorded and the resulting trend reported in FIG. 7. All the targets exposed to the NKL and YTS cells reported a considerable reduction in the fluorescent signal, compared to the control experiment.

Example 4

Detection of Functional Activity of OKT3 Monoclonal Antibody Against Jurkat Cells A method to screen for the function of antibodies produced by single hybridomas or a small number thereof was demonstrated by implementing a biological assay on an inverted open microwell platform. Muromonab-CD3 antibody, marketed by Janssen-Cilag as Orthoclone OKT3® and abbreviated here as OKT3 is a commercial therapeutic antibody having an immunosuppressant activity. The IgG2a antibody binds to CD3 receptor, an antigen present on the membrane of T-lymphocytes, such as Jurkat cells.

Hybridomas producing the OKT3 antibody were delivered to microwells of an inverted open microwell array. Using dielectrophoretic forces generated by electrodes embedded in the inverted open microwells, 1 to 4 of the hybridomas were delivered into some microwells, while some other microwells disposed in the same microchannel were not loaded with hybridomas.

Jurkat cells were stained with FLUO-4 20 µM, a green fluorescent dye used to measure the calcium concentration into living cells. When the target cell is not stimulated by the antibody, the calcium concentration remains relatively low. In contrast, binding of an anti-CD3 antibody, such as OKT3, induces a signal transduction which generates a calcium flux in the target cell followed by apoptosis of the cell. The intracellular calcium flux generated corresponds to an increase in fluorescent signal emitted by the dye.

Jurkat cells stained with FLUO-4 were delivered to all the microwells disposed along one microchannel in a number of 3 to 5 cells per microwell. Dielectrophoresis was used to direct the Jurkat cells towards the center of the microwell during their descent. In the microwells that had been previously loaded with OKT3 hybridomas, a cluster was formed of the hybridomas and the target Jurkat cells in contact with each other, while other microwells contained only target Jurkat cells to form a cluster.

Using a direct microscope, the content of each microwell was observed and a sequence of images was captured for each microwell during a period of 5-10 minutes. Fluorescence of the target Jurkat cells was measured during the time period, and the maximum value was compared to the initial value. An increase in fluorescence was calculated as the difference between the maximum and initial values divided by the initial value.

Microwells containing both hybridomas and target cells in contact, typically reported a high fluorescence increase (193% on average), while microwells where only Jurkat cells were loaded (negative control) typically reported a low or null fluorescence increase (8% on average). Detailed results are reported in Table 2.

Because all the microwells were positioned along the same microchannel, a fluid connection between different microwells, and in particular between microwells containing hybridomas and microwells not containing hybridomas, was present. The limited signal increase of the negative control demonstrates that a crosstalk signal between adjacent microwells is not present or is negligible when compared to the signal increase due to the antibody binding. We also observed that if a contact between the hybridomas and target cells was not ensured, the signal increase was typically lower. Hence, hybridoma-target cell contact preferentially ensures proper binding of the secreted antibodies to the target cell and consequent induction of a functional response by the target.

In some cases, an increase in fluorescence was not observed in the presence of the antibody secreting cell. While the reason for this is not known, it may be possible that in these cases the cells do not show a signal because only one ASC is in contact with a target, and that ASC may be in a specific stage of the cell cycle where secretion is temporarily interrupted. Despite these false negatives, the platform shows a much higher signal than negative control for most of the cases where the hybridoma is present in the microwell.

TABLE 2

| | Relative fluorescence increase | |
|---|---|---|
| EXP # | Hybridoma + Target | Only Target |
| 1 | 0% | 0% |
| 2 | 156% | 0% |
| 3 | 66% | 0% |
| 4 | 405% | 32% |
| 5 | 219% | 23% |
| 6 | 104% | 15% |
| 7 | 0% | 0% |
| 8 | 189% | 24% |
| 9 | 342% | 5% |
| 10 | 720% | 0% |
| 11 | 116% | 0% |
| 12 | 0% | 0% |
| AVERAGE | 193% | 8% |

In a different experiment we assessed the possibility to introduce the antibody through the fluid flowing in the microchannel of an inverted open microwell system. In this case the antibody can reach the bottom of the microwell because of the mixing in the microwell and/or by diffusion. We tested this concept using the same model discussed above, but in this study the Jurkat cells were initially delivered to the microwell and the OKT3 antibody was delivered to the target Jurkat cells via the microchannel fluid at a concentration of 10 µg/mL in HBSS (Hank's Buffered Salt Solution), and not by hybridoma. After introducing the antibody, an increase of green fluorescence was rapidly seen and measured as described above. Results are shown below in Table 3.

A comparison with the same assay executed outside of the chip and on a standard plate reader was performed. Results are reported in Table 3. Signal increase in the inverted open microwell is higher as the measurement is performed at the single cell level instead of measuring the average intensity change on an entire image or well.

TABLE 3

| EXP # | On-chip increase (inverted microwell) | Off-chip increase (control) (microtiter plate) |
|---|---|---|
| 1 | 170.3% | 129.91% |
| 2 | 92.7% | 77.3% |
| 3 | 273.1% | 116.36% |

Example 5

Manipulation, Isolation and Growth of Single Hybridoma Cells

To demonstrate a method for high-efficiency isolation of single antibody secreting cells, a device containing twelve inverted open microwells was used. KUL05 cells producing a murine monoclonal antibody against class II MHC antigens, were cultured in RPMI supplemented with 10% FCS. To prepare KUL05 cells for the experiment in the inverted open microwell system, the cells were resuspended in RPMI medium supplemented with HEPES 25 mM. This medium provides proper pH buffering even in absence of 5% CO2 in the atmosphere. Given the close contact of cells with the surrounding air in the inverted open microwell system a suitable medium properly buffered for these conditions is provided to the cells. Other suitable mediums include PBS and commercial products specifically designed for operating in absence of CO2.

The inverted open microwell array was mounted on a custom package which provided a direct interface of the inverted open microwell array with a standard 384-well microtiter plate, creating a small closed chamber between the inverted open microwell array and the microtiter array. With this method, the fluid contained in the wells of the microtiter plate rapidly increased the humidity of the closed chamber and provided a saturated humid environment blocking additional evaporative flow from the inverted open microwells.

RPMI supplemented with FCS 10% was placed in 12 wells of the microtiter plate and the plate was then stored at 4° C. in sterile conditions. The inverted open microwell array was sterilized with ethanol and UV rays. Prior to the experiment, the microtiter plate containing the medium at a temperature of 4° C. was positioned under the inverted open microwell array operating in a sterile environment. After package mounting, the inverted open microwell system and the microtiter plate were positioned under a direct microscope, where microwell imaging was performed from top side through the transparent material used as the top cover of the microchannels of the inverted open microwell array.

Each microchannel of the inverted open microwell array was treated with an anti-stiction coating to prevent cells from remaining attached to the microchannel walls. The coating was applied by flowing BSA 1 mM for 30 minutes and then by rinsing with PBS. Using a peristaltic pump, the KUL05 cell suspension was inserted in the microchannels of the inverted open microwell array. The KUL05 cell suspension was maintained at a temperature of about 30-37° C. throughout the entire experiment. After inserting the cells in the microchannel, the fluid was stopped and the cells sedimented into the inverted open microwells. Electrodes in each microwell were kept active in a specific configuration to align the cells along the vertical axis of the microwell during their descent to the meniscus at the lower open end of the microwell. Microwells were then inspected optically. The electrode configuration in microwells containing a single cell was changed to prevent, with proper dielectrophoretic forces, any further cell from entering the microwell. Fluid flow was then reactivated and stopped multiple times until cells were delivered to the remaining microwells.

After cell delivery, several kinds of analyses can be typically performed, according to the specific assay that needs to be implemented. In this experiment no specific assays were implemented, while an image of each microwell was captured to keep track of the number of cells docked in each microwell. A reservoir containing RPMI and HEPES 25 mM and no cells was substituted for the reservoir containing the cell suspension at the input of the peristaltic pump. Then the flow was reactivated and maintained for about 20 minutes to properly rinse the microchannel and remove all the cells not delivered to the microwells. Cells previously loaded in the microwells remained trapped on the meniscus at the air-fluid interface.

After microchannel rinse, the fluid flow was stopped, the fluid outlet closed with a plug, and a pneumatic circuit connected to the inlet. Using an electrovalve connected to a pressurized air system, a 5 millisecond pulse of sterile air at 600 millibar was injected in each microchannel. As a consequence, the content of each microwell disposed along the microchannel was transferred to a corresponding well of the underlying microtiter plate. The microtiter and the inverted open microwell array were then transferred to a sterile environment, the system was unmounted, and the microtiter plate covered with a cap and stored in a cell incubator. After 2 hours the wells of the microtiter were inspected to analyze the number of cells recovered. The same number of cells was typically detected as was previously detected in the corresponding inverted open microwell.

The microtiter plate was maintained in the cell incubator for 5-7 days. Microwells containing a single cell after the recovery were monitored daily. More than 70% of the single cells recovered from the inverted open microwell array successfully generated a monoclonal cell line during the incubation. Cell clusters from single cells were typically visible after 4-5 days.

The specification includes numerous citations to published references and patent documents, each of which is hereby incorporated by reference in its entirety.

While the invention has been illustrated and preferred embodiments described in the forgoing specification and figures, it is understood that variations and changes can be made to the preferred embodiments without deviating from the scope and spirit of the invention, for example, as embodied in the following claims.

We claim:

1. A method for screening an antibody for a desired response comprising the steps of:
    a) making available one or more inverted open microwells, wherein a microchannel having a cross sectional area of micrometer dimensions provides fluid to the one or more inverted open microwells, the microchannel having, at a first end, a fluid inlet, at a second end, a fluid outlet, wherein the fluid flows in a direction from the fluid inlet to the fluid outlet, wherein each of the one or more inverted open microwells includes an upper end open to the microchannel and a lower end open to air outside the lower end of the one or more inverted open microwells, and wherein the microchannel is located above the one or more inverted open microwells and is in fluid communication with the upper end of each of the one or more inverted open microwells and a length of the microchannel, along the direction of fluid flow is oriented perpendicularly to an axis of symmetry extending between the upper end and the lower end of each of the one or more inverted open microwells;
    b) preparing an antibody secreting cell (ASC) population;
    c) preparing a target, wherein the target can be selected from 1) microbeads prepared by binding i) the target, wherein the target is an antigen or protein, or ii) a secondary antibody specific to mouse or human IgG on the surface of the microbeads, or 2) target cells expressing a specific epitope on their membrane;
    d) inserting in the microchannel a first fluid containing the target and delivering single particles of the target to each of the one or more inverted open microwells;
    e) inserting in the microchannel a second fluid containing the ASC and delivering single ASCs to each of the one or more inverted open microwells;
    f) flowing filtered air or a mix of air and CO2 into the microchannel from the fluid inlet to the fluid outlet wherein the filtered air or mix of air and CO2 enters from the fluid inlet and exits from the fluid outlet removing the first and/or second fluid from the microchannel and completely filling the microchannel while leaving fluid in each of the one or more inverted open microwells and so defining an upper interface between air or mix of air and CO2 and fluid at the upper end of the one or more inverted open microwells and a lower interface between air or mix of air and CO2 and fluid at the lower end of the one or more inverted open microwells which is an air/fluid meniscus;
    g) wherein object pairs are kept in each of the one or more inverted open microwells at said lower interface for a time suitable for properly binding the antibody secreted by the ASC to the target, wherein the object pairs are stably retained on the air/fluid meniscus of each of the one or more inverted open microwells; and
    h) detecting a desired functional response in the target.

2. The method of claim 1, further comprising:
    allowing physiological buffer to flow into the microchannel after the step of flowing filtered air or a mix of air and CO2 into the microchannel.

3. The method of claim 2, further comprising:
    j) after the step of allowing physiological buffer to flow into the microchannel, flowing into the microchannel a fluid containing a labeled secondary antibody and allowing the secondary antibody to bind to the target; and
    k) monitoring the binding of the secondary antibody to the target.

4. The method of claim 3, wherein the labeled secondary antibody is a fluorescently labeled secondary antibody.

5. The method of claim 1, wherein the method further comprises:
    a) depositing one or more effector immune cells in close proximity to the target and the ASC, wherein the desired functional response is the ability of the effector immune cell to induce lysis of a target cell;
    b) the fluid contains complement protein(s), and where the desired functional response is complement-dependent cytolysis (CDC) of a target cell;
    c) the desired functional response is apoptosis of a target cell; or
    d) the desired response is a signaling event in a target cell.

6. The method of claim 1, wherein the ASC is a murine or human B-cell.

7. The method claim 1, wherein a plurality of antibodies is screened in an array comprising the one or more open inverted microwells, wherein each antibody of the plurality of antibodies is individually screened in different open inverted microwells of the array,
    and wherein each cell aggregate of a plurality of cell aggregates is stably retained at the air fluid meniscus of a different open inverted microwell in the array.

8. The method of claim 7, wherein the plurality of cell aggregates comprises aggregates of target cell-effector cell couples.

9. The method of claim 7, further comprising the step of releasing onto a substrate the retained cell(s) from each of the one or more inverted open microwells, where the released cell(s) is a viable cell(s).

10. The method of claim 9, wherein the released cell is selected from:
    a) the ASC, wherein the ASC is identified as producing an antibody that binds to a target cell and induces complement-mediated cytolysis (CDC) of the target cell;
    b) the ASC, wherein the ASC is identified as producing an antibody that induces antibody-dependent cell mediated cytolysis (ADCC) of a target cell; and
    c) the ASC, wherein the ASC is identified as producing an antibody that induces apoptosis of a target cell.

11. The method of claim 1, wherein one or more cells are stably retained on an air/fluid meniscus of the one or more inverted open microwells, or wherein one or more cells form an aggregate that is stably maintained on an air/fluid meniscus of the one or more inverted open microwells.

* * * * *